United States Patent
Milo et al.

(10) Patent No.: US 6,949,114 B2
(45) Date of Patent: Sep. 27, 2005

(54) SYSTEMS, METHODS, AND COMPOSITIONS FOR ACHIEVING CLOSURE OF VASCULAR PUNCTURE SITES

(75) Inventors: Charles F. Milo, Atherton, CA (US); Olexander Hnojewyj, Saratoga, CA (US); Timothy J McCoy, San Carlos, CA (US); Bruce S Addis, Redwood City, CA (US)

(73) Assignee: NeoMend, Inc., Irvine, CA (US)

( * ) Notice: Subject to any disclaimer, the term of this patent is extended or adjusted under 35 U.S.C. 154(b) by 0 days.

(21) Appl. No.: 09/780,843

(22) Filed: Feb. 9, 2001

(65) Prior Publication Data

US 2001/0047187 A1 Nov. 29, 2001

Related U.S. Application Data

(63) Continuation-in-part of application No. 09/283,535, filed on Apr. 1, 1999, now Pat. No. 6,458,147, which is a continuation-in-part of application No. 09/188,083, filed on Nov. 6, 1998, now Pat. No. 6,371,975.

(51) Int. Cl.[7] .............................................. A61B 17/08
(52) U.S. Cl. ........................................ 606/213; 604/15
(58) Field of Search ................................ 606/213, 216, 606/196, 159, 215; 604/285–288, 507–509; 623/1.12, 1.13, 1.42, 1.43

(56) References Cited

U.S. PATENT DOCUMENTS

| | | | |
|---|---|---|---|
| 4,101,380 A | 7/1978 | Rubinstein et al. ........... 195/63 |
| 4,161,948 A | 7/1979 | Bichon ....................... 128/156 |
| 4,464,468 A | 8/1984 | Avrameas et al. .......... 435/177 |
| 4,839,345 A | 6/1989 | Doi et al. |
| 5,051,406 A | 9/1991 | Satoh .......................... 514/21 |
| 5,087,244 A | * 2/1992 | Wolinsky et al. ...... 604/103.01 |
| 5,129,882 A | 7/1992 | Weldon et al. ................ 604/96 |
| 5,207,670 A | 5/1993 | Sinofsky |
| 5,252,714 A | 10/1993 | Harris et al. ............. 530/391.9 |
| 5,269,755 A | * 12/1993 | Bodicky ................ 604/103.01 |
| 5,279,565 A | * 1/1994 | Klein et al. ................. 604/105 |
| 5,318,524 A | 6/1994 | Morse et al. ................. 604/82 |
| 5,383,896 A | 1/1995 | Gershony et al. ........... 606/213 |
| 5,403,278 A | 4/1995 | Ernst et al. ................... 604/60 |
| 5,410,016 A | 4/1995 | Hubbell et al. ............. 528/354 |
| 5,419,765 A | 5/1995 | Weldon et al. ................ 604/96 |
| 5,423,742 A | * 6/1995 | Theron ........................ 604/28 |
| 5,462,529 A | * 10/1995 | Simpson et al. ........ 604/101.04 |
| 5,514,379 A | 5/1996 | Weissleder et al. ......... 424/426 |
| 5,520,885 A | 5/1996 | Coelho et al. .............. 422/101 |
| 5,529,577 A | 6/1996 | Hammerslag ............... 606/214 |
| 5,567,435 A | 10/1996 | Hubbell et al. ............. 424/426 |
| 5,583,114 A | 12/1996 | Barrows et al. .............. 514/21 |

(Continued)

FOREIGN PATENT DOCUMENTS

| | | |
|---|---|---|
| WO | WO 96/11671 | 10/1994 |
| WO | WO 97/22371 | 12/1995 |
| WO | WO 99/07417 | 8/1997 |
| WO | WO 99/14259 | 9/1997 |
| WO | WO 99/45964 | 3/1998 |
| WO | WO 00/09087 | 8/1998 |
| WO | WO 09/09199 | 8/1998 |
| WO | WO 00/33764 | 12/1998 |

*Primary Examiner*—Julian W. Woo
*Assistant Examiner*—Victor Nguyen
(74) *Attorney, Agent, or Firm*—Ryan Kromholz & Manion, S.C.

(57) ABSTRACT

Systems and methods convey a closure material into a catheter to seal a puncture site in a blood vessel. The closure material comprises a mixture of first and second components which, upon mixing, undergo a reaction to form a solid closure material composition. The systems and methods assure ease of delivery and effective mixing of the components to create an in situ barrier at the puncture site.

7 Claims, 14 Drawing Sheets

U.S. PATENT DOCUMENTS

| | | | |
|---|---|---|---|
| 5,601,602 A | 2/1997 | Fowler | 606/213 |
| 5,611,775 A * | 3/1997 | Machold et al. | 604/103.01 |
| 5,626,601 A | 5/1997 | Gershony et al. | 606/194 |
| 5,626,863 A | 5/1997 | Hubbell et al. | 424/426 |
| 5,653,730 A | 8/1997 | Hammerslag | 606/214 |
| 5,672,662 A | 9/1997 | Harris et al. | |
| 5,676,689 A | 10/1997 | Kensey et al. | 606/213 |
| 5,725,498 A | 3/1998 | Janzen et al. | 604/51 |
| 5,733,563 A | 3/1998 | Fortier | 424/422 |
| 5,739,208 A | 4/1998 | Harris | 525/54.1 |
| 5,759,194 A | 6/1998 | Hammerslag | 606/114 |
| 5,782,860 A * | 7/1998 | Epstein et al. | 606/213 |
| 5,791,352 A | 8/1998 | Reich et al. | 606/213 |
| 5,824,015 A | 10/1998 | Sawyer | 606/214 |
| 5,843,124 A | 12/1998 | Hammerslag | 606/214 |
| 5,844,016 A | 12/1998 | Sawhney et al. | 606/314 |
| 5,858,746 A | 1/1999 | Hubbell et al. | 606/214 |
| 5,874,500 A | 2/1999 | Rhee et al. | 606/213 |
| 5,900,245 A | 5/1999 | Sawhney et al. | 424/426 |
| 5,900,461 A | 5/1999 | Harris | 525/54.11 |
| 5,922,009 A | 7/1999 | Epstein et al. | |
| 5,932,462 A | 8/1999 | Harris et al. | |
| 5,935,147 A | 8/1999 | Kensey et al. | |
| 5,936,035 A | 8/1999 | Rhee et al. | |
| 5,942,209 A | 8/1999 | Leavitt et al. | |
| 5,951,583 A | 9/1999 | Jensen et al. | |
| 5,951,589 A | 9/1999 | Epstein et al. | |
| 5,986,043 A | 11/1999 | Hubbell et al. | 528/354 |
| 5,990,237 A | 11/1999 | Bentley et al. | 525/54.2 |
| 6,007,613 A | 12/1999 | Izoret | 106/160.1 |
| 6,022,336 A * | 2/2000 | Zadno-Azizi et al. | 604/101.05 |
| 6,022,361 A | 2/2000 | Epstein et al. | |
| 6,051,248 A | 4/2000 | Sawhney et al. | |
| 6,060,582 A | 5/2000 | Hubbell et al. | |
| 6,083,524 A | 7/2000 | Sawhney et al. | |
| 6,152,943 A | 11/2000 | Sawhney | |
| 6,162,241 A | 12/2000 | Coury et al. | |
| 6,165,201 A | 12/2000 | Sawhney et al. | |
| 6,177,095 B1 | 1/2001 | Sawhney et al. | |
| 6,179,862 B1 | 1/2001 | Sawhney | 606/214 |
| 6,217,549 B1 * | 4/2001 | Selmon et al. | 604/104 |
| 6,221,049 B1 * | 4/2001 | Selmon et al. | 600/585 |
| 6,235,000 B1 * | 5/2001 | Milo et al. | 604/164.01 |
| 6,371,975 B2 * | 4/2002 | Cruise et al. | 606/214 |
| 6,398,798 B2 * | 6/2002 | Selmon et al. | 606/159 |

* cited by examiner

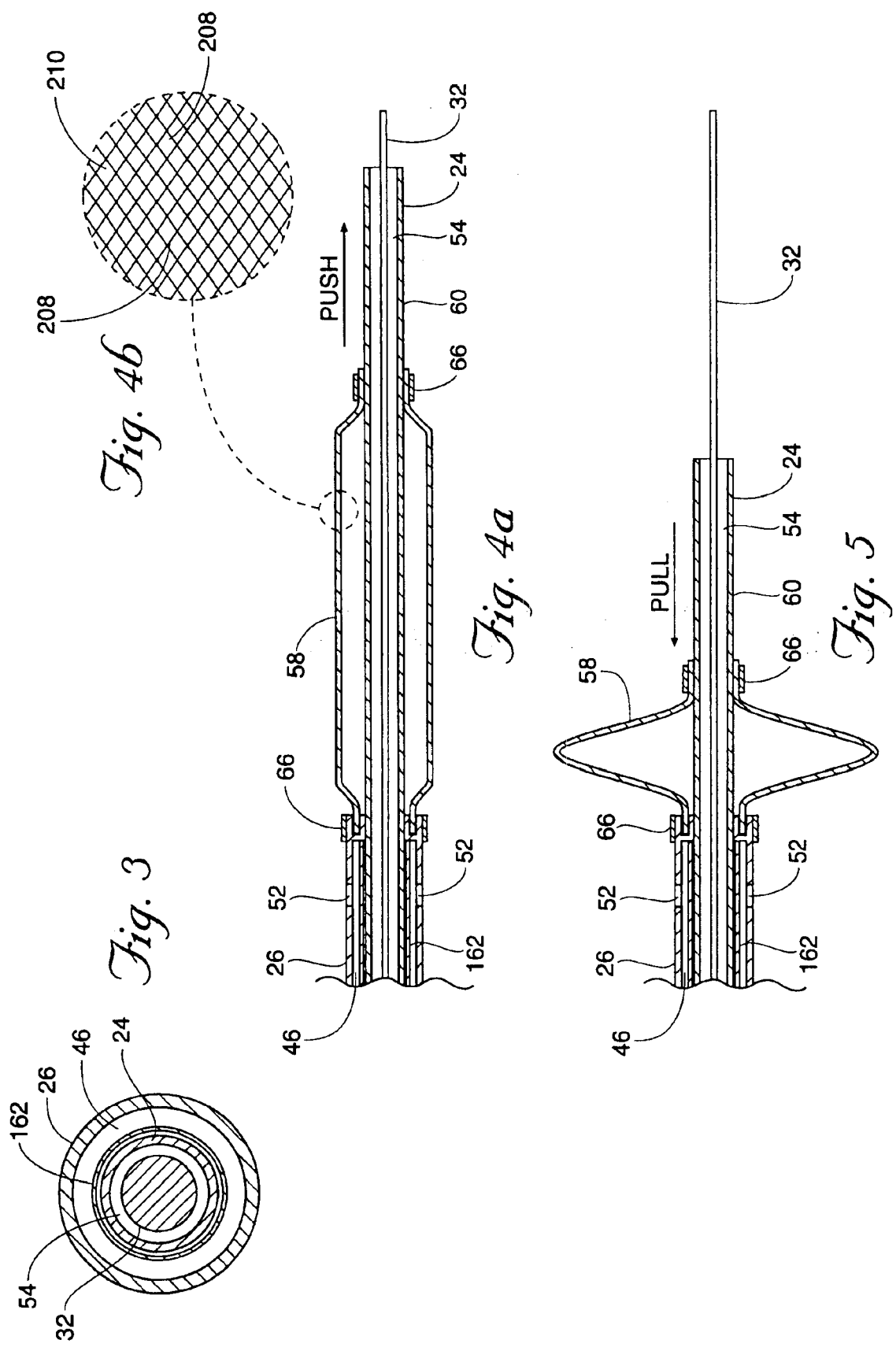

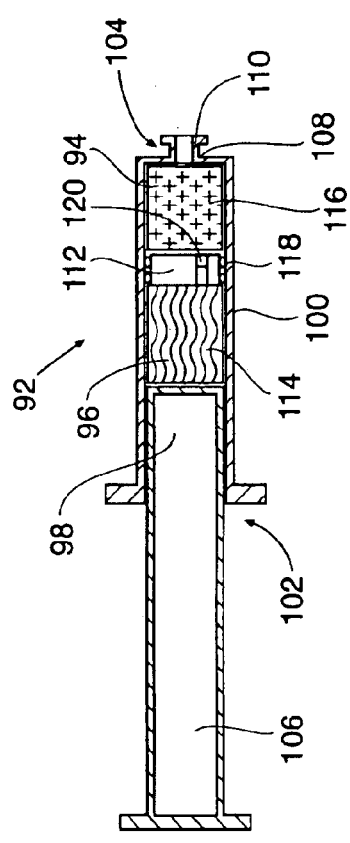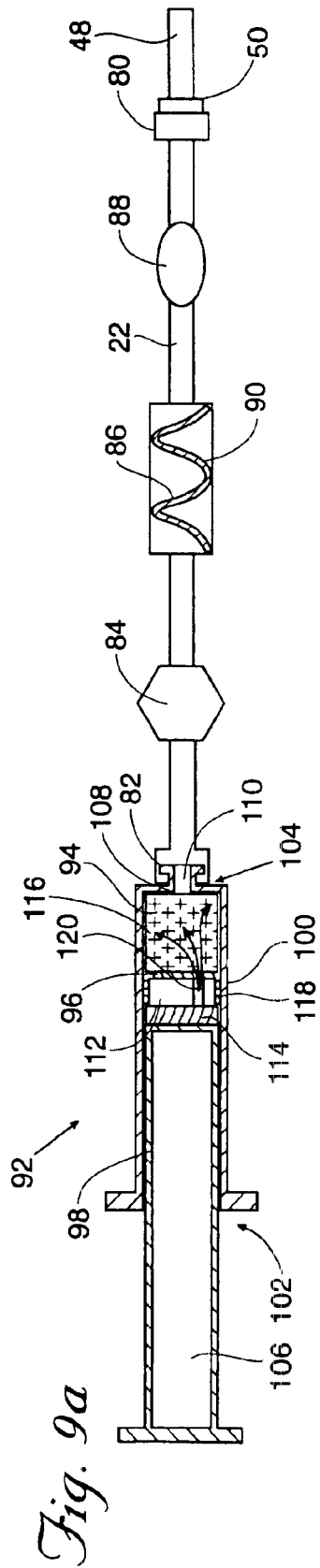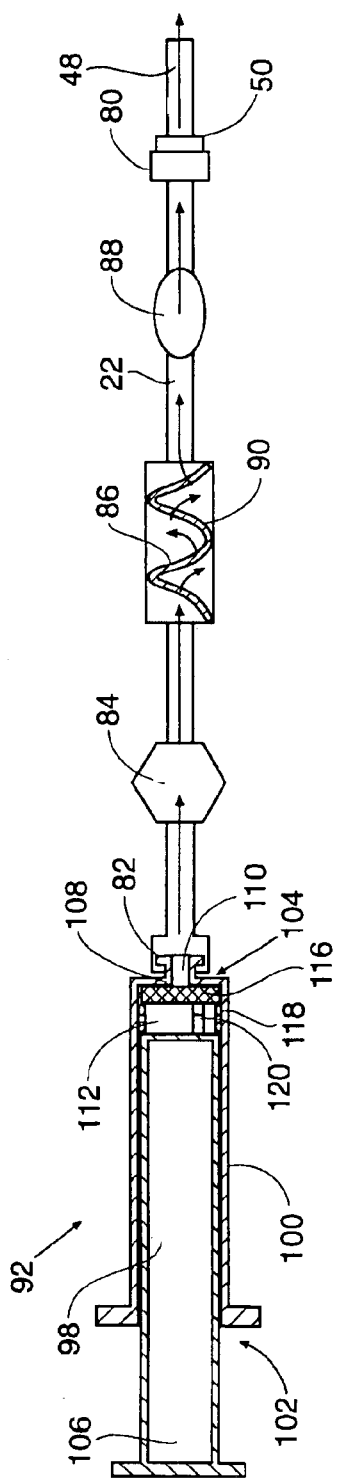

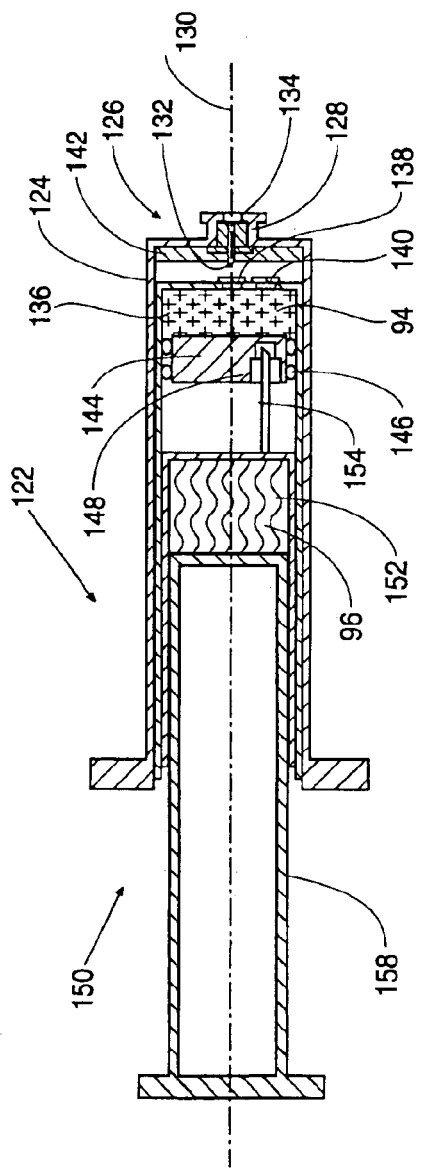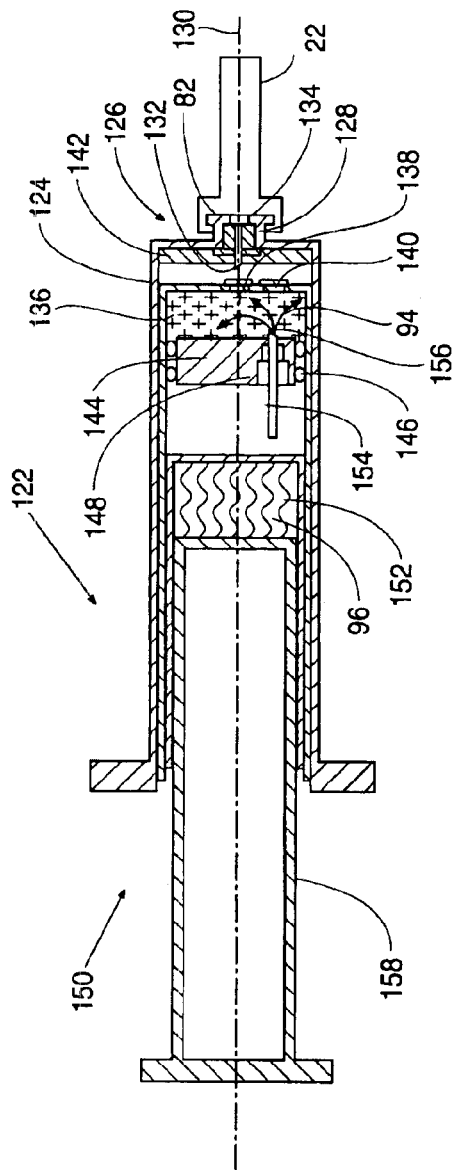

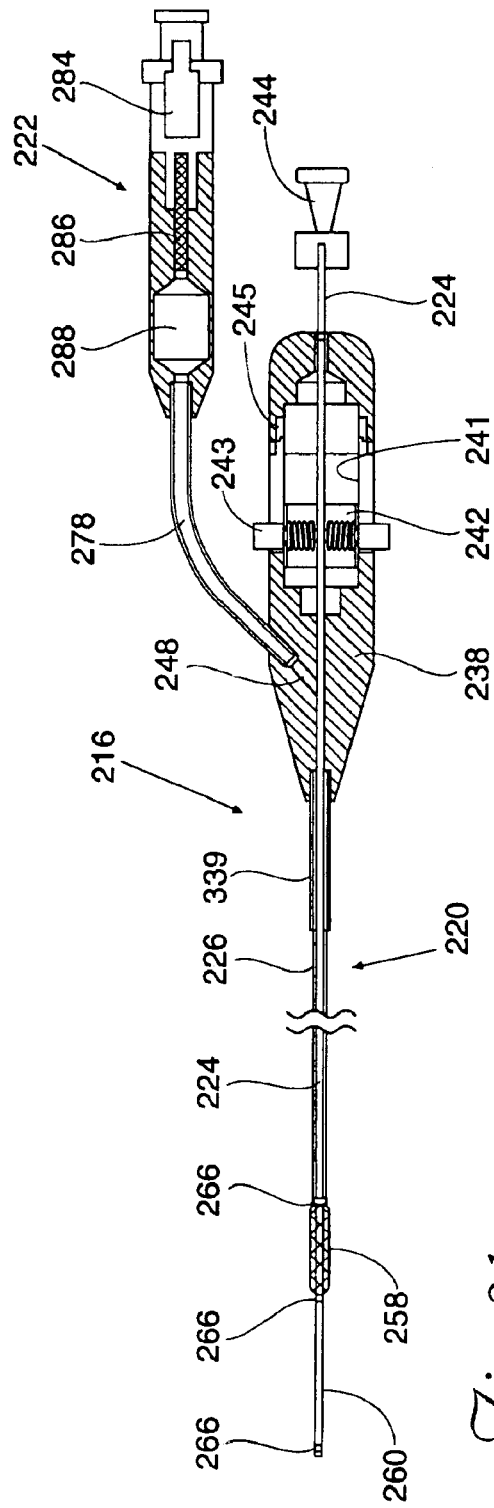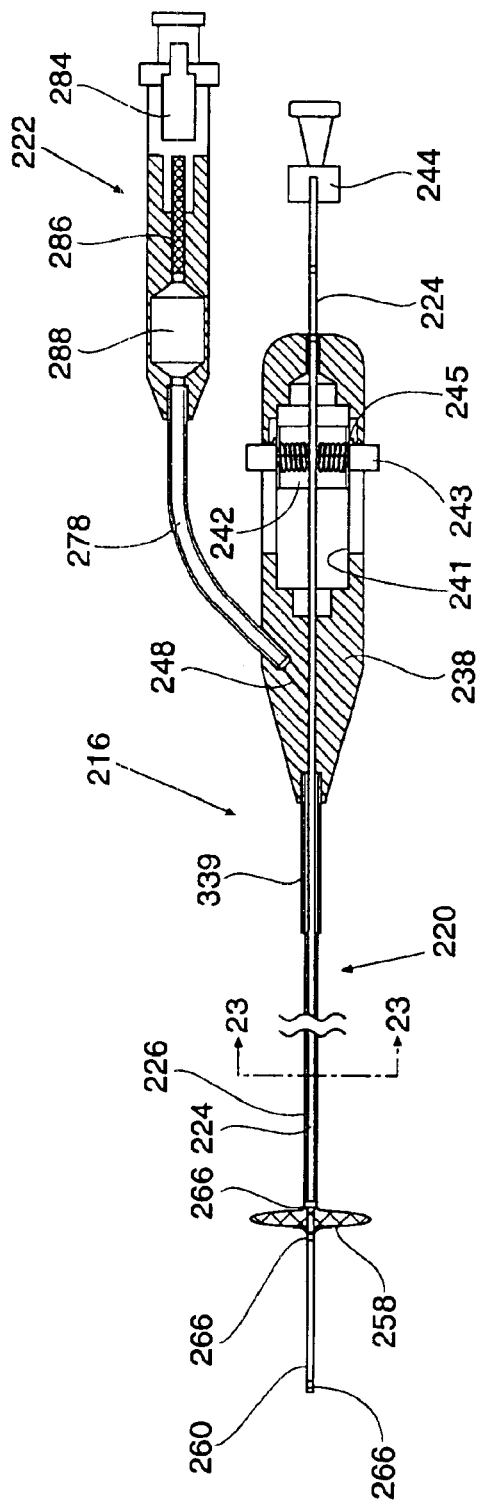

SYSTEMS, METHODS, AND COMPOSITIONS FOR ACHIEVING CLOSURE OF VASCULAR PUNCTURE SITES

RELATED APPLICATION

This application is a continuation-in-part of U.S. patent application Ser. No. 09/283,535, filed Apr. 1, 1999, now U.S. Pat. No. 6,458,147 and entitled "Compositions, Systems, And Methods For Arresting or Controlling Bleeding or Fluid Leakage in Body Tissue," which is itself a continuation-in-part of U.S. patent application Ser. No. 09/188,083, filed Nov. 6, 1998 now U.S. Pat. No. 6,371,975 and entitled "Compositions, Systems, and Methods for Creating in Situ, Chemically Cross-linked, Mechanical Barriers."

FIELD OF THE INVENTION

The invention generally relates to the systems and methods for delivering biocompatible materials to body tissue to affect desired therapeutic results.

BACKGROUND OF THE INVENTION

There are many therapeutic indications today that pose problems in terms of technique, cost efficiency, or efficacy, or combinations thereof.

For example, following an interventional procedure, such as angioplasty or stent placement, a 5 Fr to 9 Fr arteriotomy remains. Typically, the bleeding from the arteriotomy is controlled through pressure applied by hand, by sandbag, or by C-clamp for at least 30 minutes. While pressure will ultimately achieve hemostasis, the excessive use and cost of health care personnel is incongruent with managed care goals.

Various alternative methods for sealing a vascular puncture site have been tried. For example, collagen plugs have been used to occlude the puncture orifice. The collagen plugs are intended to activate platelets and accelerate the natural healing process. Holding the collagen seals in place using an anchor located inside the artery has also been tried. Still, patient immobilization is required until clot formation stabilizes the site. Other problems, such as distal embolization of the collagen, rebleeding, and the need for external pressure to achieve hemostatis, also persist.

As another example, devices that surgically suture the puncture site percutaneously have also been used. The devices require the practice of fine surgical skills to place needles at a precise distance from the edges of the puncture orifice and to form an array of suture knots, which are tightened and pushed from the skin surface to the artery wall with a knot pusher, resulting in puncture edge apposition.

There remains a need for fast and straightforward mechanical and chemical systems and methods to close vascular puncture sites and to accelerate the patient's return to ambulatory status without pain and prolonged immobilization.

There also remains a demand for biomaterials that improve the technique, cost efficiency, and efficacy of these and other therapeutic indications.

SUMMARY OF THE INVENTION

The invention provides systems and methods for introducing a closure material to seal a puncture site in a blood vessel. The closure material comprises a mixture of first and second components which, upon mixing, react to form a solid closure material composition.

According to one aspect of the invention, the systems and methods provide a catheter having a distal end and at least one nozzle located adjacent the distal end. A catheter lumen in the catheter conveys the first and second components for dispensing through the nozzle. An expandable structure is carried on the catheter distal to the nozzle. According to this aspect of the invention, the structure comprises an open configuration, allowing blood flow through the structure.

The systems and methods deploy the catheter through a tissue puncture track to locate the structure within the blood vessel. The systems and methods expand the structure within the blood vessel to resist its outward passage through the puncture site. The systems and methods locate the nozzle outside the blood vessel adjacent the puncture site by pulling on the catheter to bring the expanded structure in contact with an interior wall of the blood vessel.

Due to its open configuration, the structure permits blood flow through it, thereby presenting a minimal disruption of blood flow in the vessel during its use. Due to its open configuration, the structure can be deployed in an expanded state within the artery prior to being seated against the interior of the vessel wall, with minimal disruption of blood flow. This allows the physician to proceed with the deployment and positioning of the structure within the vessel in a deliberate fashion, without being rushed due to ancillary considerations of attendant blood flow disruption.

According to another aspect of the invention, the systems and methods establish a fluid path communicating, at one end, with one or more dispensers containing the first and second compositions and, at another end, with a catheter, as just described or possessing another construction. The systems and methods bring the first and second components into a mixed condition in the fluid path before entering the catheter. The systems and methods retain a residual volume of the first and second components in the mixed condition within a composition test chamber located in the fluid path, while allowing another volume of the first and second components to enter the catheter in the mixed condition. According to this aspect of the invention, the systems and methods can monitor the reaction forming the solid closure material with reference, at least in part, to the residual volume retained in the composition test chamber.

In one embodiment, the composition test chamber comprises a transparent structure enclosing the residual volume. In this arrangement, the reaction forming the solid closure material composition can be visually gauged.

In one embodiment, the composition test chamber comprises a flexible pouch-like structure enclosing the residual volume. In this arrangement, the reaction forming the solid closure material composition can be tactilely gauged.

In one embodiment, air is vented in the fluid path.

According to another aspect of the invention, the systems and methods dispense the closure material to a catheter using an applicator. The applicator includes a barrel having an applicator end and a dispensing end. There is a plunger on the applicator end for advancement into the barrel toward the dispensing end. There are also first and second compartments formed within the barrel. The systems and methods house the first component prior to use in one of the first and second compartments. The systems and methods house the second component prior to use in the other one of the first and second compartments.

According to this aspect of the invention, the systems and methods operate the plunger in a first advancement mode. In this mode, the plunger dispenses the first component from the one compartment into the other compartment to form a mixture of the first and second components within the other compartment.

Also according to this aspect of the invention, the systems and methods operate the plunger in a second advancement mode. In this mode, the plunger dispenses the mixture from the dispensing end.

In one embodiment, the first component is housed in a liquid form.

In one embodiment, the second component is housed in a solid form.

In one embodiment, the second component is housed in a lyophilized form.

Features and advantages of the inventions are set forth in the following Description and Drawings, as well as in the appended Claims.

BRIEF DESCRIPTION OF THE DRAWINGS

FIG. 3 is a cross section view of the inner and outer catheter bodies that comprise the catheter assembly shown in FIG. 2, taken generally along section line 3—3 in FIG. 2;

FIG. 4A is an enlarged section view of the distal end of a catheter assembly that forms a part of the vascular puncture site access assembly shown in FIG. 1, showing the expandable structure carried by the assembly in a collapsed condition;

FIG. 4B is an enlarged view of the wall of the expandable structure shown in FIG. 4A, showing its open or woven configuration that allows blood flow through the structure;

FIG. 5 is an enlarged section view of the distal end of a catheter assembly that forms a part of the vascular puncture site access assembly shown in FIG. 1, showing the expandable structure carried by the assembly in an expanded condition;

FIG. 8 is a section view of a unitary applicator that shows one embodiment of the formative component assembly shown in FIG. 1, in which a solid component and a liquid component for the closure composition are contained prior to use;

FIGS. 9A and 9B are section views showing the operation of the unitary applicator shown in FIG. 8;

FIG. 10 is a section view of a unitary applicator that shows another embodiment of the formative component assembly shown in FIG. 1, in which a solid component and a liquid component for the closure composition are contained prior to use;

FIGS. 11A to 11C are section views showing the operation of the unitary applicator shown in FIG. 10;

FIG. 21 is a side section view an alternative embodiment of a vascular site access assembly, comprising a catheter assembly and a component introducer/mixer assembly that, in use, delivers a biocompatible material closure composition to a vascular puncture site, showing the expandable structure carried by the catheter assembly in a collapsed or stowed condition;

FIG. 22 is a side section view of the vascular site access assembly shown in FIG. 21, showing the expandable structure carried by the catheter assembly in an expanded condition;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

I. System Overview

Figure 1:
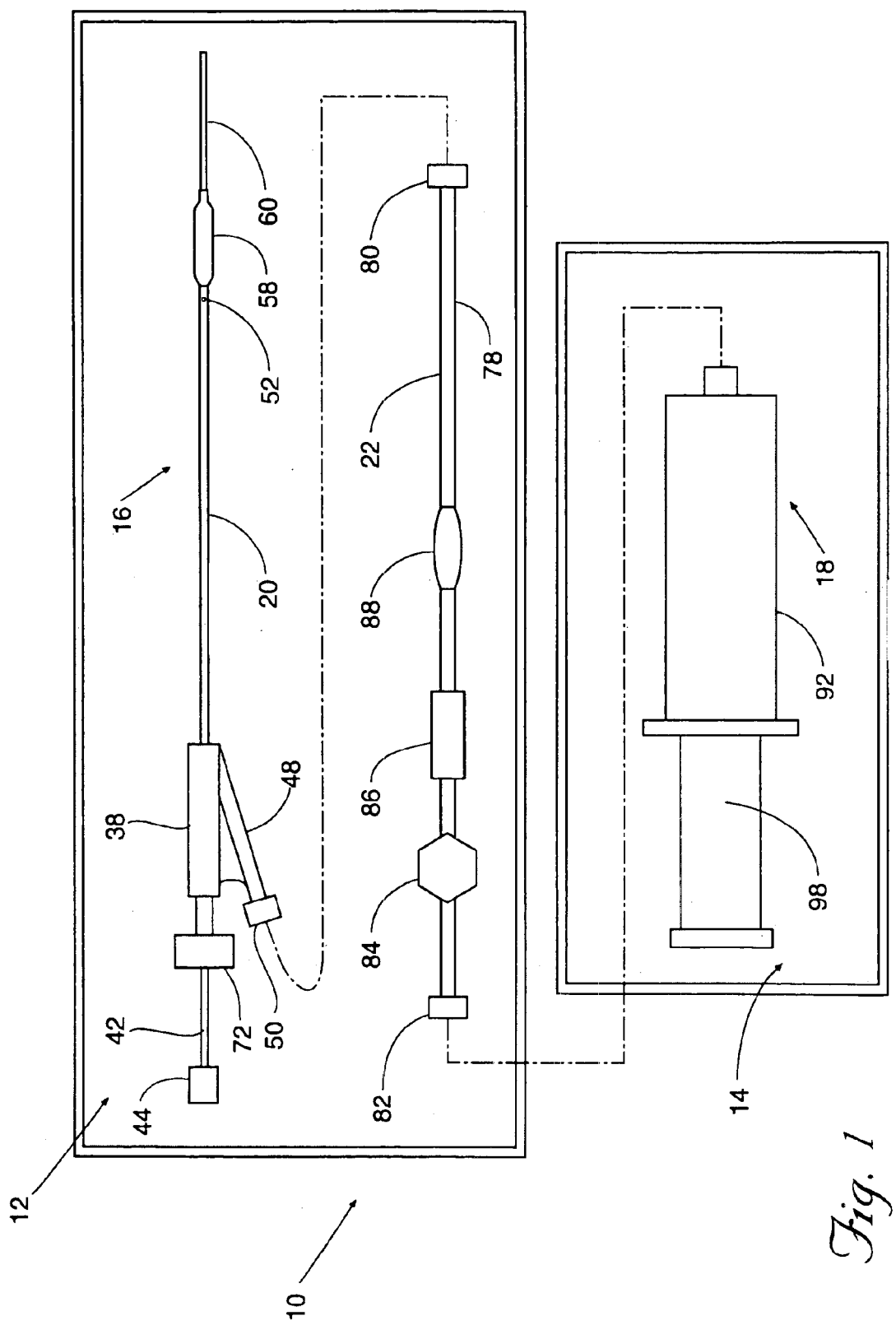
FIG. 1 is a view of a system of functional instruments for closure of a vascular puncture site e.g., following a vascular access procedure, comprising a vascular puncture site access assembly, to gain transcutaneous access to the vascular puncture site for the purpose of delivering a biocompatible material closure composition, and a formative component assembly, to house the components of the biocompatible material closure composition prior to use.

FIG. 1 shows a system 10 of functional instruments for closure of a vascular puncture site e.g., following a vascular access procedure.

As will be described in greater detail, the instruments of the system 10 are, during use, deployed in a purposeful manner to gain transcutaneous access to a vascular puncture site. The instruments of the system 10 are manipulated to place a biocompatible material composition outside the blood vessel at the puncture site. The biocompatible material composition produces a solid, three dimensional matrix that closes the puncture site.

In a preferred embodiment, the biocompatible material composition is comprised of two or more formative components which are mixed in a liquid state while being delivered by the system 10 transcutaneously to the puncture site. Upon mixing, the formative components react, in a process called "gelation," to transform in situ from the liquid state, to a semi-solid (gel) state, and then to the biocompatible solid state.

In the solid state, the composition takes the form of a non-liquid, three-dimensional network. Desirably, the solid material composition exhibits adhesive strength (adhering it to adjacent tissue), cohesive strength (forming a mechanical barrier that is resistant to blood pressure and blood seepage), and elasticity (accommodating the normal stresses and strains of everyday activity). These properties provide an effective closure to the vascular puncture site.

The solid material composition is also capable of transforming over time by physiological mechanisms from the solid state to a biocompatible liquid state, which can be cleared by the body, in a process called "degradation."

As FIG. 1 shows, in one embodiment, the system 10 can be contained, prior to use, in two functional kits 12 and 14.

The first kit 14 contains a vascular puncture site access assembly 16. The purpose of the access assembly 16 is to gain transcutaneous access to the vascular puncture site for the purpose of delivering the biocompatible material composition.

The second kit 14 contains a formative component assembly 18. The purpose of the formative component assembly 18 is to house the components of the biocompatible material composition prior to use. As will be described in greater detail later, these components are mixed and delivered by the access assembly 16 to the puncture site.

The kits 12 and 14 can take various forms. In the illustrated embodiment, each kit 12 and 14 comprises a sterile, wrapped assembly.

A. The Access Assembly

As FIG. 1 shows, the access assembly 16 comprises a catheter assembly 20 and a component introducer/mixer assembly 22.

1. The Catheter Assembly

Figure 2:
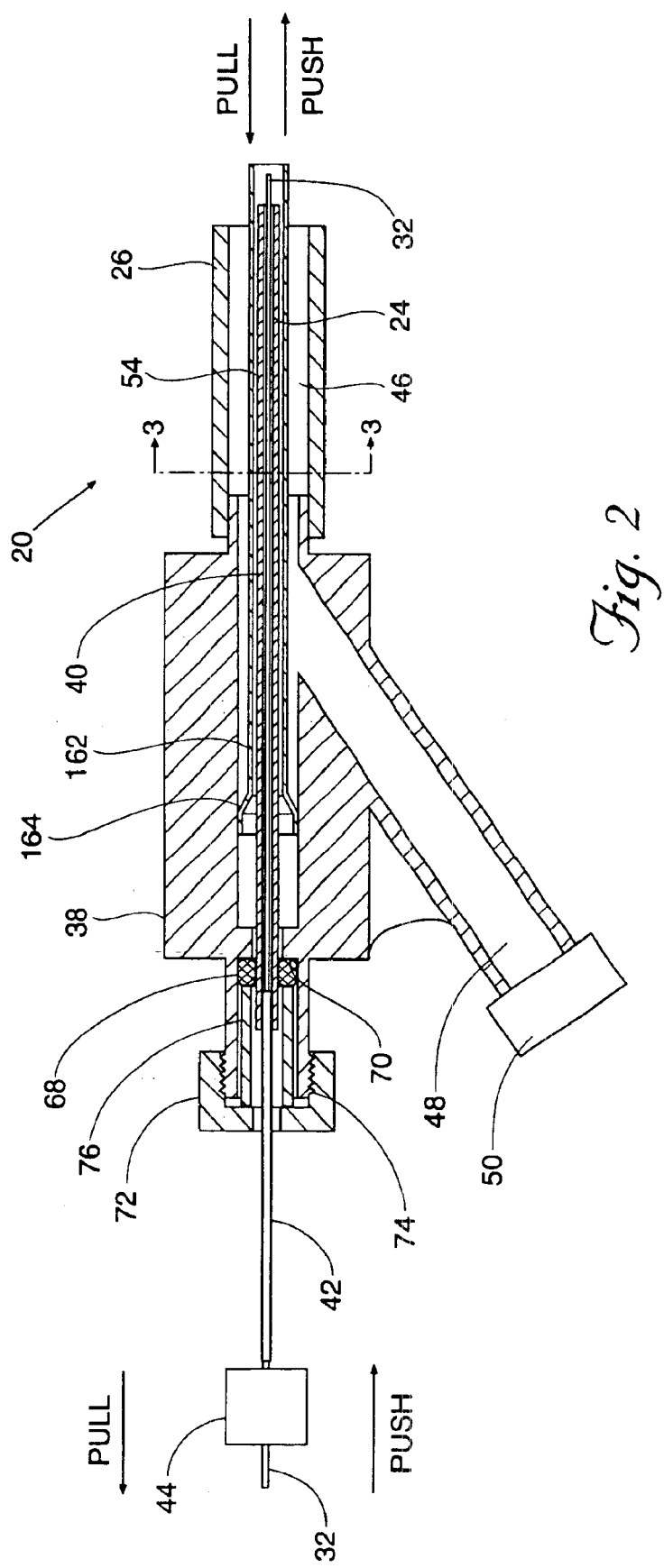
FIG. 2 is an enlarged section view of the proximal end of a catheter assembly that forms a part of the vascular puncture site access assembly shown in FIG. 1.

The catheter assembly 20 comprises a flexible inner catheter body 24 that is slidably carried within a flexible outer catheter body 26 (see FIGS. 2 to 4). The catheter bodies 24 and 26 can be constructed, for example, using standard flexible, medical grade plastic materials, like vinyl, nylon, poly(ethylene), and poly(urethane). The outside diameter of the outer catheter body 26 can vary, e.g., from 6 Fr. to 10 Fr.

The diameter of the outer catheter body 26 is sized to seal the tissue track through which it is introduced. The tissue track typically will have been previously formed by a vascular introducer or cannula 28 (see FIG. 12), through which the desired therapeutic or diagnostic instrument 30 is first introduced (typically over a guide wire 32) through a puncture site 36 into the vessel, e.g., to perform coronary angioplasty. After performing the intended procedure, the instrument 30 and introducer 28 are withdrawn (see FIG. 13), leaving the puncture site 36 and the tissue track 34. The outside diameter of the outer catheter body 26 is selected to match the outside diameter of the vascular introducer 28, so that the outer catheter body 26, when deployed, will block substantial flow of blood from the puncture site 36 up the tissue track 34.

The proximal end of the outer catheter body 26 is secured, e.g., by adhesive, to a luer fitting on the distal end of a preformed y-shaped adapter 38 (see FIG. 3). The adapter 38 serves as a handle for the entire catheter assembly 20.

The proximal end of the inner catheter body 24 (see FIG. 2) extends beyond the proximal end of the outer catheter body 26 into a lumen 40 formed in the y-shaped adapter 38. In the illustrated embodiment, a generally rigid tubular extender 42 is coupled to the distal end of the inner catheter body 24 within the lumen 40. The extender 42 projects outside the proximal end of the adapter 38. The exposed end of the extender 42 desirably carries an enlarged gripping surface 44, which can be conveniently gripped by the physician between the thumb and index finger.

The extender 42 provides structural rigidity to the proximal end of the inner catheter body 24, and also serves as a force applicator for the inner catheter body 24. In response to the application of a pushing force on the extender 42, the inner catheter body 24 slides in a distal direction within the outer catheter body 26. In response to the application of a pulling force on the fitting, the inner catheter body 24 slides in a proximal direction within the outer catheter body 26.

The interior diameter of the outer catheter body 26 (see FIGS. 3 to 5) is larger than the exterior diameter of the inner catheter body 24. An interior passage 46 is thereby defined between them. A port 48 on the adaptor/handle 38 (see FIG. 2) communicates with the passage 46. The port 48 terminates with a luer fitting 50, to which the component introducer/mixer assembly 22 is coupled (see FIG. 7), as will be described later. In this way, the liquid components of the material composition are conveyed into the passage 46 (as will be also described later).

Figure 6A:
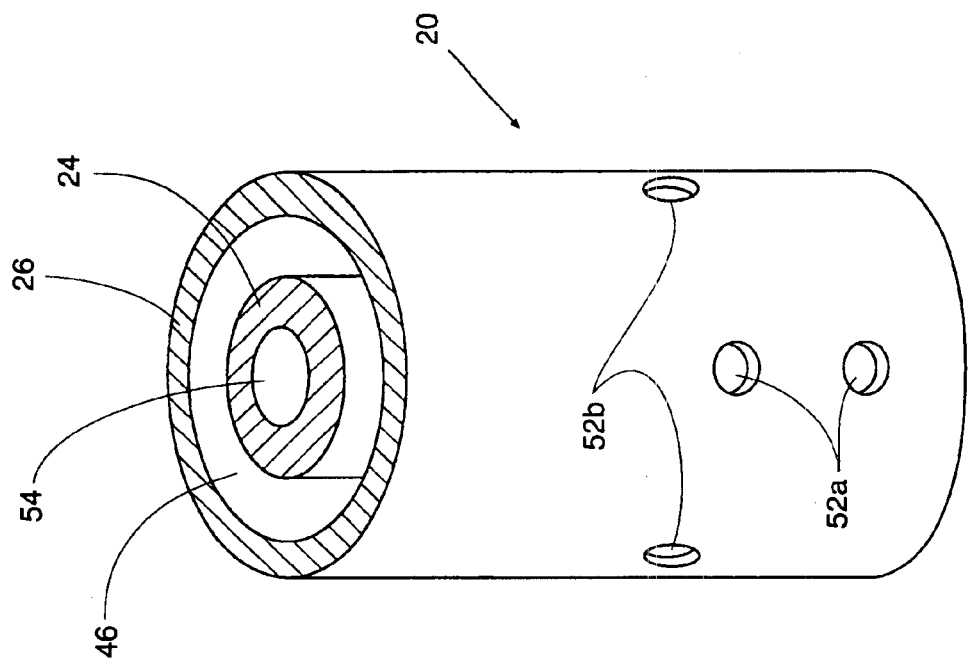
FIGS. 6A and 6B are perspective views of alternatively arrays of composition delivery nozzles located on the catheter assembly that forms a part of the vascular puncture site access assembly shown in FIG. 1.
Figure 6B:
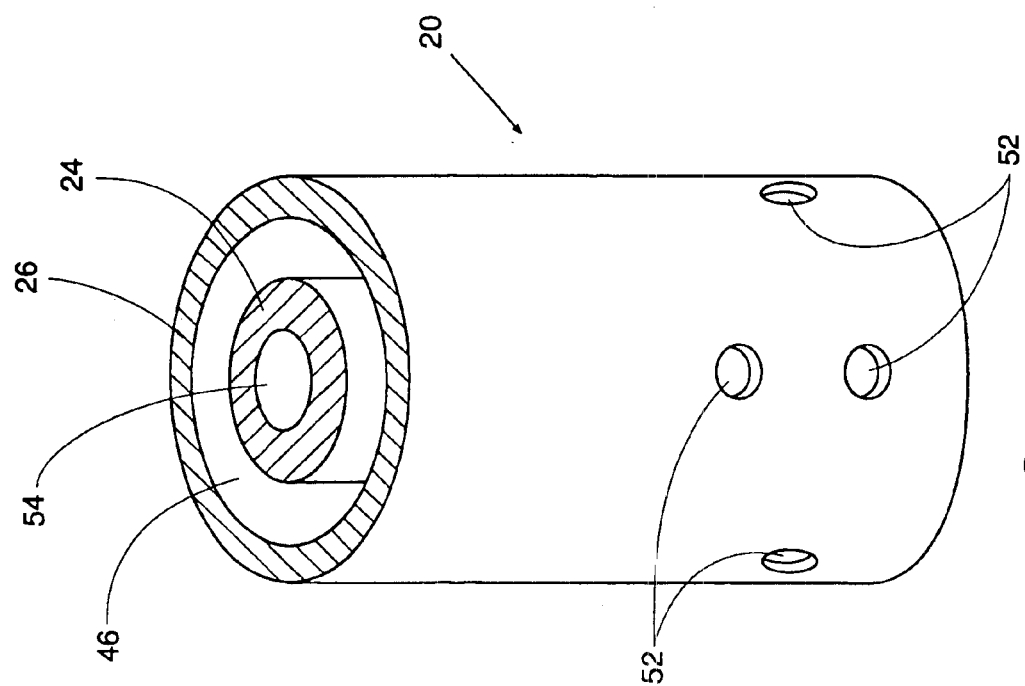

The liquid components exit the passage 46 through one or more nozzles 52 formed near the distal end of the outer catheter body 26 (see FIGS. 4, 5, and 6A/B). The nozzles 52 can be arranged in different delivery patters. In one embodiment (as FIG. 6A shows), a array of nozzles 52, circumferentially spaced apart, is provided. In another embodiment (as FIG. 6B shows), the nozzles 52A and 52B are spaced apart along the axis of the outer catheter body 26, as well as being staggered to face different directions about the axis.

The diameter of the nozzles 52 can also vary (e.g., from 0.02" to 0.035"). The nozzles 52 can all share the same diameter. Alternatively, the nozzles 52 can have different diameters, to create preferential flow patterns (the liquid composition following the path of less flow resistance in preference to a path of greater flow resistance). Further details regarding the rationale for arranging and sizing the nozzles 52 will be provided later.

Figure 12:
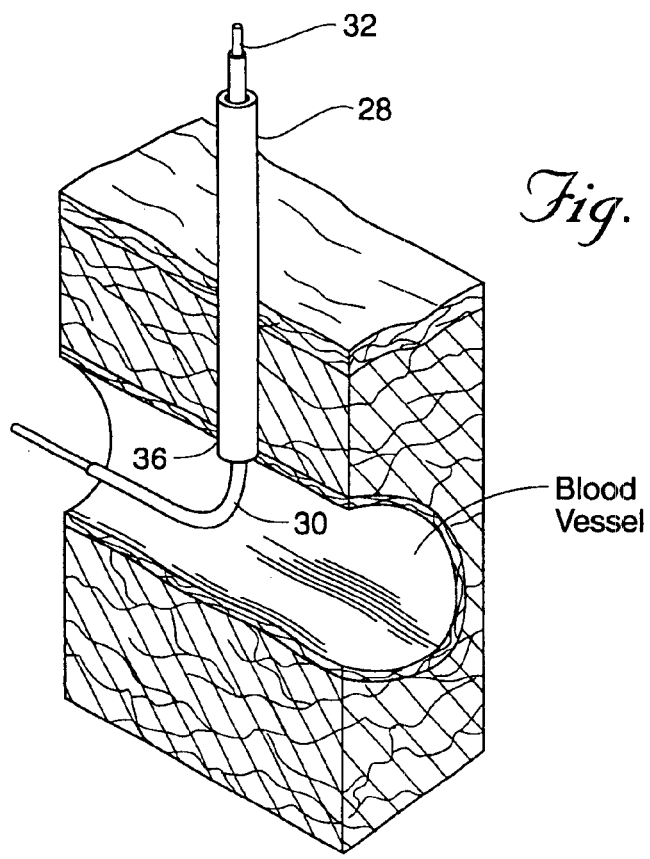
FIG. 12 is a diagrammatic view of blood vessel puncture site formed to enable the delivery of a diagnostic or therapeutic instrument through a vascular sheath and over a guide wire.
Figure 13:
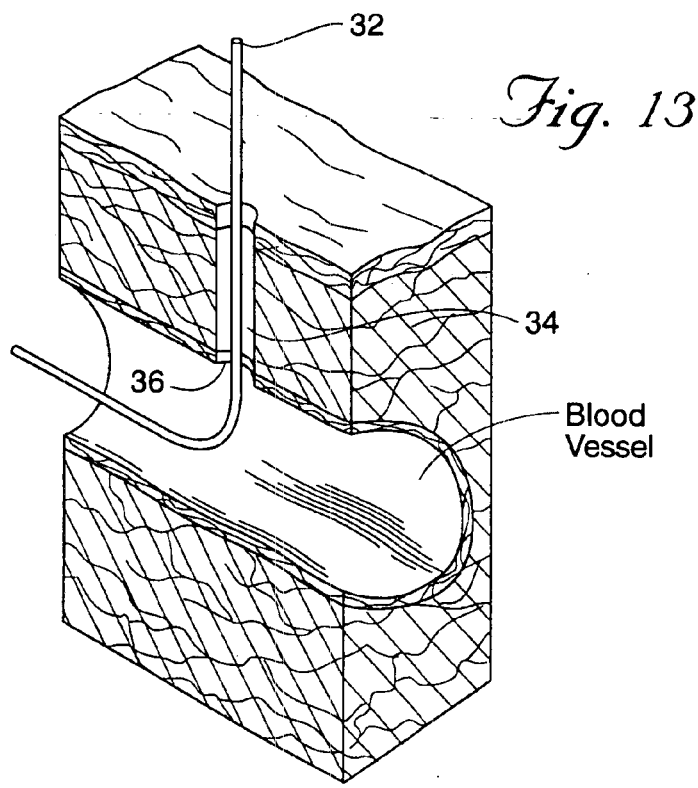
FIG. 13 is a diagrammatic view of the blood vessel puncture site shown in FIG. 12, after removal of the diagnostic or therapeutic instrument and vascular sheath, keeping the guide wire deployed.
Figure 14:
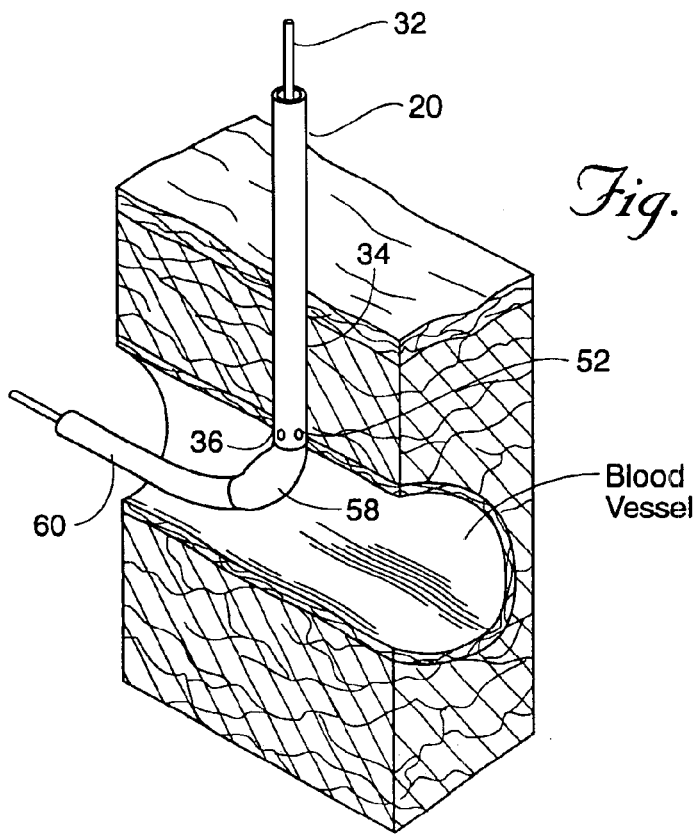
FIG. 14 is a diagrammatic view of the blood vessel puncture site shown in FIG. 13, during deployment of the vascular puncture site access assembly shown in FIG. 1, the access assembly being deployed over the guide wire with the expandable structure in a collapsed condition.

The inner catheter body 24 itself defines an interior lumen 54 within the interior passage 46 (see FIG. 3). The extender 42, too, includes an interior bore, so that the passage formed by the lumen 54 extends along the entire effective length of the inner catheter body 24 and extender 42. As will be described in greater detail later (and as shown in FIGS. 2 to 5), the lumen 54 accommodates passage of a guide wire 32 to aid in the deployment of the catheter assembly 20. The guide wire 32 typically will have been previously introduced subcutaneously, through a wall of the vessel, to guide passage of the therapeutic or diagnostic instrument 30 through the vascular introducer 28 into the vessel (as FIG. 12 shows). While the instrument 30 and vascular introducer 28 are withdrawn following the procedure, the guide wire 32 desirably is kept in place (as FIG. 13 shows). In this way, the distal end of the catheter assembly 20 can be passed over the same guide wire 32 into the blood vessel (as FIG. 14 shows).

It is desired that the nozzles 52 reside outside the blood vessel when the material composition is introduced. To help locate the nozzles 52 outside the blood vessel, the catheter assembly 20 includes an expandable structure 58 located near to and distally of the nozzles 52 (see FIGS. 4A and 5).

In the illustrated embodiment, the wall 210 of the structure 58 desirably comprises an open or woven or braided structure comprising interlaced or intersecting strands or threads 208 (see FIG. 4B), e.g., made from an inert biocompatable polymeric material, such as nylon. Alternatively, the outer catheter body 26 can itself be slotted at circumferentially spaced locations to form the structure 56.

The proximal end of the structure 58 is secured, e.g., by adhesive, to the interior of the distal end of the outer catheter body 26. In the illustrated embodiment, the distal end of the structure 58 occupies the passage 46 between the inner and outer catheter bodies 24 and 26 downstream of the nozzles 52, but it does not impede the sliding movement of the inner catheter body 24 in this region.

A thin wall tube 162 (e.g., extruded from PET or polyimide material with a wall thickness of about 0.001 inch) can be provided to envelope the inner catheter body 24 within the y_shaped adaptor 38 and outer catheter body 26. The thin wall tube 162 permits sliding movement of the inner catheter body 24 within it, but prevents composition material in the passage 46 from contacting the inner catheter body 24 to adhesively bind the moveable inner catheter body 24 to the stationary outer catheter body 26.

In the illustrated embodiment, the thin wall tube extends from a position within with the y-shaped adaptor lumen 40 (see FIG. 2) upstream of the composition material port 48, to the junction between the inner catheter tube proximal end of the structure 58 joins the inner catheter tube 24 (see FIGS. 4 and 5). As FIG. 2 also shows, the proximal end 164 of the thin wall tube 162 is enlarged and sealed to the interior of the lumen 40 in a upstream flow direction to the port 48. The proximal end 164 of the thin wall tube 162 thereby impedes the backflow of composition material and other fluids in the lumen 40 toward the proximal end of the y-shaped adaptor/handle 38.

Figure 7:
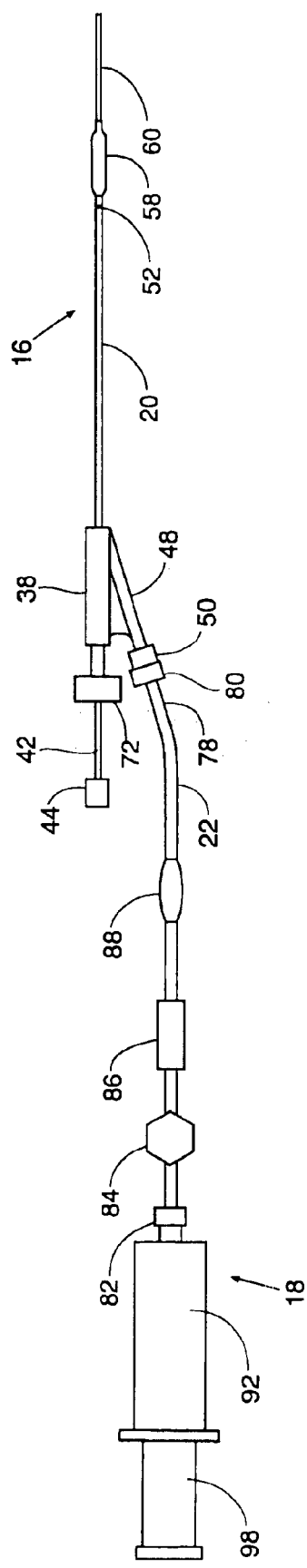
FIG. 7 shows the components of the vascular puncture site access assembly coupled to the formative component assembly, ready for use.

The distal end of the structure 58 is secured, e.g., by adhesive or a shrink-fit sleeve, to a region of the inner catheter body 24 that extends beyond the outer catheter body 26 (as FIG. 7 shows).

Figure 15:
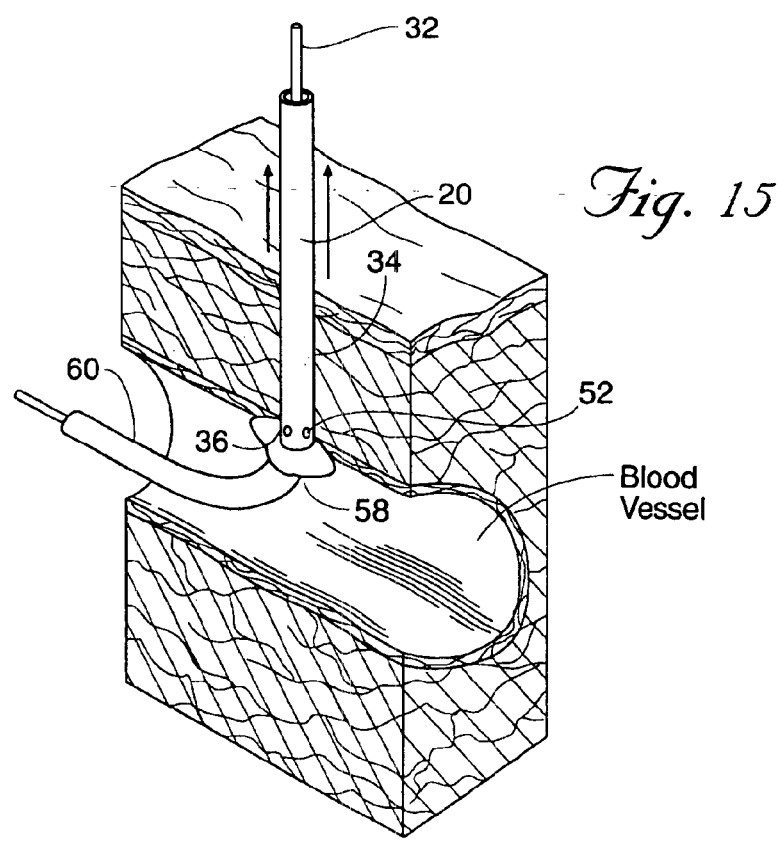
FIG. 15 is a diagrammatic view of the blood vessel puncture site shown in FIG. 14, with the vascular puncture site access assembly deployed and the expandable structure in an expanded condition serving as a positioner within the blood vessel for the closure composition delivery nozzles outside the blood vessel.

In the illustrated embodiment, the inner catheter body 24 extends a distance distally beyond the structure, forming a leader 60. In use, the leader 60 is located inside the blood vessel immediately interior to the puncture site 36 (see FIGS. 14 and 15). In use, the array of nozzles 52 is located outside the blood vessel exterior to the puncture site 36 (as FIG. 15 shows). Sliding movement of the inner catheter body 24 relative to the outer catheter body 26 serves to mechanically expand and collapse the structure 58 (as FIGS. 4 and 5 show), so that this desired positioning of the nozzles 52 and leader 60 can be achieved.

More particularly, the application of a pushing force upon the inner catheter body 24 (via the extender 42) moves the distal end of the structure 58 (which is secured to the movable inner catheter body 24) away from the proximal end of the structure 58 (which is secured to the fixed the outer catheter body 26). As shown in FIG. 4A, the structure 58 lengthens to reach is full normal length. As the structure 58 lengthens, the body of the structure 58 flattens, being urged radially inward into a collapsed, low profile configuration, shown in FIG. 4A, and also in FIG. 1. This configuration possesses an outside diameter that is about the same as the outside diameter of the outer catheter body 26.

When in the low profile condition, the structure 58 follows the leader 60 over the guide wire 32 into the vessel, posing little resistance (see FIG. 14).

The application of a pulling force upon the inner catheter body 24 (via the extender 42) moves the distal end of the structure 58 (which is secured to the movable inner catheter body 24) toward the proximal end of the structure 58 (which is secured to the fixed the outer catheter body 26). As shown in FIG. 5, the structure 58 shortens as the ends approach one another. As the structure 58 shortens, the body of the structure 58 bows, being urged radially outward into an expanded, disc-like configuration, shown in FIG. 5. This configuration possesses an outside diameter greater than the outside diameter of the outer catheter body 26.

In this configuration, the structure 58 forms a positioner. In use (see FIG. 15), the positioner resists passage of the leader 60 back through the puncture site 36 in response to rearward tension placed by the physician along the catheter assembly 20. Rearward tension along the catheter assembly 20 seats the positioner against the interior of vessel wall at the puncture site 36. The positioner serves to position the nozzles 52 at a proper distance outside the vessel. The positioner also serves to support the puncture site 36 inside the vessel while the liquid barrier material 64 is introduced outside the vessel through the nozzles 52 (see FIG. 16). The presence of the thin wall tube 162 isolates the inner catheter body 24 from contact with the liquid barrier material in the passage 46. The desired sliding motion of the inner catheter body 24 is thereby preserved, and the presence of the liquid barrier material in the passage 24 does not adhesively lock the structure 58 in the expanded condition.

Since, in the illustrated embodiment, the structure 58 possesses a wall that is open or woven, the structure 58 permits blood flow through it, thereby presenting a minimal disruption of blood flow in the vessel during use. Due to the open or woven configuration of the structure 58, the positioner can be deployed in an expanded state within the artery prior to being seated against the interior of the vessel wall, with minimal disruption of blood flow. This allows the physician to proceed with the deployment and positioning of the structure 58 within the vessel in a deliberate fashion, without being rushed due to ancillary considerations of attendant blood flow disruption.

Desirably (see FIGS. 4 and 5), radiopaque marker bands 66 are secured to the proximal and distal ends of the structure 58. In this way, the physician can fluroscopically gauge the distance between the ends of the structure 58 and, thereby, assess the position and configuration of the structure 58 near the puncture site 36.

An elastomeric gasket 68 (see FIG. 2) preferably rests in a seat 70 in the lumen 40 in the y-adaptor/handle 38. The gasket 68 and seat 70 form a hemostatic valve, resisting passage of blood or other fluids out the proximal end of the y-adaptor/handle 38. The extender 42 passes through the gasket 68 (see FIG. 2). The elastomeric material of the gasket 68 conforms to and thereby seals about the extender 42. The gasket 68 will impose a frictional drag, which will normally resist movement of the inner catheter body 24 absent the application of a direct pushing or pulling force to the extender 42. The frictional drag provides tactile feedback to the physician when expanding or collapsing the structure 58.

Desirably (as FIG. 2 also shows), a rotatable luer cap 72 rotates on threads 74 about the proximal end of the y-adaptor/handle 38. A stem 76 on the cap 72 extends into the lumen 40. Upon clockwise rotation of the cap 72, the stem 76 places successively more pressure against the gasket 68 within the seat 70, to thereby enhance the sealing effect of the hemostatic valve. Clockwise rotation of the cap 72 will also increase the magnitude of the frictional drag imposed by the gasket 68 upon the extender 42. By clockwise rotation of the cap 72, the physician can selectively "lock" the configuration of the structure 58 in a desired expanded condition, or a desired collapsed condition, or any desired in between condition.

2. The Component Introducer/Mixer Assembly

Before mixing, the components for the material composition are housed in the formative component assembly 18 contained in the kit 14 (see FIG. 1), which will be described in greater detail later. As FIG. 1 shows, the introducer/mixer assembly 22 includes a length of flexible tubing 78 having a distal luer fitting 80 that couples to the formative component assembly 18 and a proximal luer fitting 82 that couples to the port 48 of the y-adaptor/handle 38 (see FIG. 7).

In the illustrated embodiment (as best shown on FIGS. 1 and 7), the introducer/mixer assembly 22 also includes, communicating with the tubing 78 in the direction of flow from the formative component assembly 18 to the y-adaptor/handle 38, an in-line air vent 84, an in-line mixing chamber 86, and an in-line composition test chamber 88.

The air vent 84 can take various forms. In the illustrated embodiment, the air vent 84 takes the form of a conventional, vented 0.22 μm hydrophobic filter used, e.g., for in-line IV applications. These filters are commercially available, e.g., from Filtertek.

The components of the material composition come into contact in the liquid state in the in-line mixing chamber 86 before entering the catheter assembly 20. In this way, effective mixing can be achieved outside the catheter assembly 20 that is not dependent upon the dimensions or lengths of the flow paths within the catheter assembly 20. The mixing chamber 86 preferably includes interior mixing structures 90 (see FIGS. 9A and 9B), which create flow conditions to mechanically enhance and accelerate the mixing effect, so that static mixing of the components occurs as they flow through the mixing chamber 86 in transit to the catheter assembly.

The form and arrangement of the interior mixing structures 90 can vary. For example, the mixing chamber 86 can includes an array of interior funnel walls with staggered interruptions, or baffle walls arranged perpendicular to the flow path with staggered interruptions or arranged about a hub in a spiral pattern (as FIGS. 9A and 9B show). Various different configurations for the mixing structures 90 are shown in greater detail in copending U.S. patent application Ser. No. 09/187,384, filed Nov. 6, 1998 and entitled "Systems and Methods for Applying Cross-Linked Mechanical Barriers," which is incorporated herein by reference.

The in-line composition test chamber 88 provides a tactile gauge by which the physician can remotely ascertain the approximate stage of the in situ reaction of the composition material within the body. In the process of conveying the composition material to the puncture site, the test chamber 88 collects and retains an external residual volume of composition material. In the test chamber 88, the residual volume will undergo transform from a liquid state, to a semi-solid state, and to a solid state, at approximately the same pace as the in situ reaction at the puncture site. The test chamber 88 desirably possesses a transparent balloon or pouch-like structure, which encloses the residual composition material volume. The physician can squeeze or otherwise handle the test chamber 88, to tactilely assess the physical properties of the composition material, e.g., by viewing the flow characteristics of the composition within the chamber 88 and/or by ascertaining the resistance of the composition to manual compression. In this way, the physician is able to remotely monitor the physical state of the material composition.

B. The Formative Component Assembly

The components forming the material composition can vary. Generally speaking, however, the components will include a solid component and a liquid component, which serves as a diluent for the solid component. Mixing of these two components initiates a chemical reaction, by which the liquid mixture transforms into a solid composition. It is the purpose of the formative component assembly to keep the solid component and liquid component separate until the instance of use.

The formative component assembly 18 can comprise individual syringes in which the components are separately contained. Further details of this arrangement are disclosed in copending U.S. patent application Ser. No. 09/187,384, filed Nov. 6, 1998 and entitled "Systems and Methods for Applying Cross-Linked Mechanical Barriers," which has already been incorporated herein by reference.

An alternative arrangement (see FIG. 8) provides a unitary applicator 92 in which a solid component 94 and a liquid component 96 are kept separate in sealed interior compartments. A single actuator assembly 98, operated by the physician, brings the two components 94 and 96 together within the applicator 92, by placing the solid component 94 into suspension within the liquid component 96. The actuator 98 also expels the liquid suspension into the introducer/mixer assembly 22 for further mixing and delivery to the catheter assembly 20, as just described.

In the embodiment shown in FIG. 8, the applicator 92 includes a barrel 100 having an actuator end 102 and a dispensing end 104. A syringe plunger 106 is carried in the actuator end 102 for axial movement within the barrel 100 in response to conventional manipulation. The dispensing end 104 includes an outlet port 108 with a luer fitting 110. Prior to use, the outlet port 108 is sealed, e.g., using a peelable foil seal. At the instance of use, the foil seal is peeled away, and the luer fitting 110 is coupled to the distal luer fitting 80 of the introducer/mixer assembly 22 (as FIG. 9A shows).

A internal barrier 112 is carried within the barrel 100 (see FIG. 8). The barrier 112 divides the barrel 100 into two interior compartments 114 and 116. The first compartment 114 extends between the barrier 112 and the syringe plunger 106 and contains the liquid component 96 in sterile, liquid form. The second compartment 116 extends between the barrier 112 and the dispensing port 108 and contains the solid component 94 in sterile, lyophilized form.

The barrier 112 is peripherally sealed, e.g., by o-rings 118, to the sidewall of the barrel 100, thereby normally preventing communication between the two compartments 114 and 116. The barrier 112 includes a one-way or check valve 120, which opens to allow flow of liquid component 96 from the first compartment 114 into the second compartment 116, occasioned by the increased fluid pressure in the first compartment 114 relative to the second compartment 116. The one-way valve 120 does not permit an opposite flow from the second compartment 116 into the first compartment 114. The increase in fluid pressure in the first compartment 114 is created (as will soon be described) by advancement of the syringe plunger 106 in the first compartment 114 toward the barrier 112.

The barrier 112 is also movable toward the dispensing port 108 along the axis of the barrel 100 in response to an external force. This external force (as will also be soon described) is created by advancement of the syringe plunger 106 into contact with the barrier 112.

In use (see FIG. 9A), the physician couples the dispensing port 108 to the distal luer fitting 80 of the introducer/mixer assembly 22. The physician applies thumb pressure to syringe plunger 106 in conventional fashion to advance the plunger 106 within the first compartment 114 toward the barrier 112. Advancement of the plunger 106 increases the pressure in the first compartment 114, which opens the one-way valve 120. As FIG. 9A shows, the liquid component 96 in the first compartment 114 is urged by advancement of the syringe plunger 106 through the valve 120 into the second compartment 116. In the second compartment 116, the liquid component 96 mixes with the solid component 94.

Advancement of the syringe plunger 106 through the first compartment 114, expelling its liquid contents, will, in time, being the terminus of the syringe plunger 106 into direct contact with the barrier 112 (see FIG. 9B). Further advancement of the syringe plunger 106 will move the barrier 112 in tandem with the plunger 106 into the second compartment 116. As FIG. 9B shows, advancement of the plunger-driven barrier 112 through the second compartment 116 expels the suspension of liquid component and solid component through the dispensing port 108 into the introducer/mixer assembly 22. The in-line vent device 84 vents air from the suspension, and the mixing chamber 86 brings the liquid and solid components 94 and 96 into intimate further contact to start the chemical reaction between the two.

Another embodiment of a unitary applicator 122 is shown in FIG. 10. The applicator 122 includes a barrel housing 124 having a dispensing end 126. The dispensing end 126 includes an outlet port 128 positioned along the center line axis 130 of the barrel housing 124. The outlet port 128 carries a puncture spike 132 with a luer fitting 134. The luer fitting 134 is intended to be coupled, during use, to the distal luer fitting 80 of the introducer/mixer assembly 22 (see FIG. 11A).

A mixing chamber 136 is concentrically carried within the barrel housing 124 in the dispensing end 126. The mixing chamber 136 includes first and second normally foil sealed ports 138 and 140. The first port 138 is aligned along the common center line 130 of the barrel housing 124 and the mixing chamber 136 with the puncture spike 132 carried in the dispensing end 126 of the barrel housing 124. As FIG. 10 shows, the mixing chamber 136 is positioned such that the puncture spike 132 is normally spaced from the first foil sealed port 138. An elastomeric gasket 142 surrounds the puncture spike 132 and occupies the space between the foil sealed port 138 of the mixing chamber 136 and the dispensing end 126 of the barrel housing 124. As will be described later, the mixing chamber 136 is movable within the barrel housing 124 against the gasket 142, toward the dispensing end 126 of the barrel housing 124, to pierce the foil sealed port 138 with the puncture spike 132, to open flow communication between the mixing chamber 136 and the dispensing end 126 of the barrel housing 124 (see FIG. 11C).

The second normally foil sealed port 140 in the mixing chamber 136 is offset from the common center line axis 130 of the barrel housing 124 and the mixing chamber 136. Further details of the function of the second port 140 will be described later.

As FIG. 10 shows, an internal barrier 144 is carried within the mixing chamber 136. The barrier 144 is peripherally sealed, e.g., by o-rings 146, to the sidewall of the mixing chamber 136. The barrier 144 includes a septum 148 that is offset from the center axis 130 of the barrel housing 124. The septum 148 is aligned with the second port 140 of the mixing chamber 136. The septum 148 carries a conventional needle sealing material.

The barrier 144 is movable within the mixing chamber 136 in response to hydraulic pressures or an externally applied force, as will be described later.

The barrel housing 124 also includes an actuator end 150. A diluent chamber 152 is carried concentrically within the barrel housing 124 in the actuator end 150.

One end of the diluent chamber 152 extends concentrically into the mixing chamber 136. This end is closed, except for a needle 154 that extends outward of the diluent chamber 152 into the mixing chamber 136. The needle 154 is offset from the common center line axis 130 of the barrel housing 124 and the diluent chamber 152 and extends in alignment with the septum 148 of the barrier 144 and the second port 140 of the mixing chamber 136.

As FIG. 10 shows, the diluent chamber 152 and the barrier 144 are positioned before use such that the end of the needle 154 is positioned within the septum 148. As will be described later, the diluent chamber 152 is moveable within the mixing chamber 136 to cause the needle 154 to pass through the septum 148 and to enter the mixing chamber 136 on the opposite side of the barrier 144 (i.e., the side facing the dispensing end 126) (see FIG. 11A). This opens communication between the diluent chamber 152 and the mixing chamber 136 on this side of the barrier 144. The end of the needle 154 desirable possesses a fluid spray tip 156.

The other end of the diluent chamber 152 is open and receives a syringe plunger 158. The syringe plunger 158 is movable in conventional fashion through the diluent chamber 152.

As FIG. 10 shows, the solid component 94 occupies the mixing chamber 136 between the barrier 144 and the foil sealed ports 138 and 140. The barrier 144 and the foil sealed ports 138 and 140 serve to seal this material 94 within the mixing chamber 136 prior to use. The mixing chamber 136, together with the barrier 144 and prefilled with the solid component 94, are assembled as a unit and inserted into the barrel housing 124.

The liquid component 96 occupies the diluent chamber 152 between the terminus of the syringe plunger 158 and the closed end of the diluent chamber 152. Desirably, the syringe plunger 158 and the diluent chamber 152 with the offset needle 154 (and prefilled with the liquid component 96 using standard sterile fill techniques) are assembled as a unit and inserted into the barrel housing 124.

In use (see FIG. 11A), the physician couples the dispensing port 128 to the distal luer fitting 80 of the introducer/mixer assembly 22. The physician applies thumb pressure to syringe plunger 158 in conventional fashion. Advancement of the plunger 158 causes the needle 154 to advance through the septum 148 into the mixing chamber 136 on the opposite side of the barrier, occupied by the solid component 94. Continued advancement of the plunger 158 causes liquid component in the diluent chamber 152 to enter the mixing chamber 136 through the fluid spray tip 156 of the needle 154. The solid and liquid components mix.

Figure 11B:
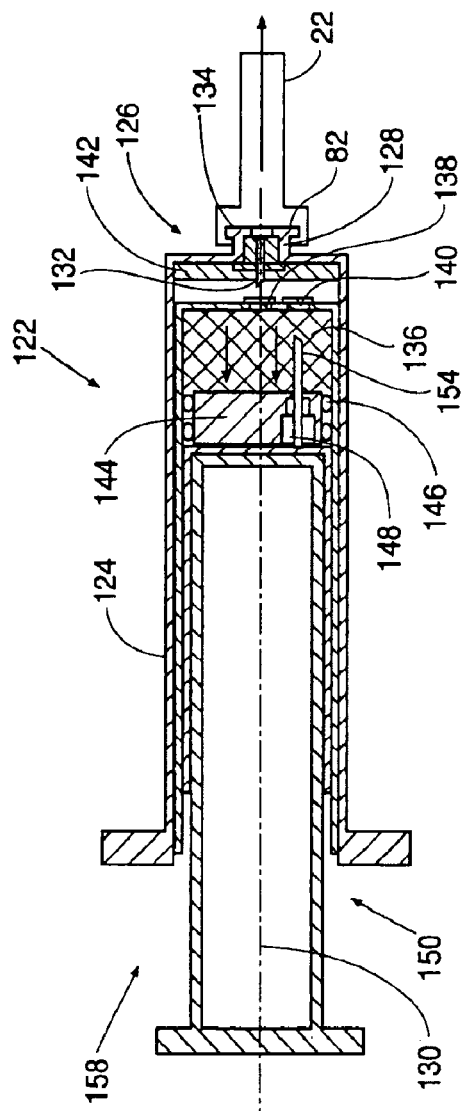

Continued advancement of the plunger 158, causing increasing volume of liquid component 96 to be delivered into the mixing chamber 136, creates hydraulic pressures upon the barrier 144. As FIG. 11B shows, these hydraulic pressures move the barrier 114 away from the dispensing end 126 of the barrel housing 124 and toward the end of the diluent chamber 152. As the transfer of liquid component 96 into the mixing chamber 136 continues, the barrier 144 contacts the end of the diluent chamber 152 (see FIG. 11B). At this point, the liquid contents of the diluent chamber 152 have entered the mixing chamber 136. No air has been transferred into the mixing chamber 136, as the transfer of the liquid component 96 was accomplished under vacuum.

Figure 11C:
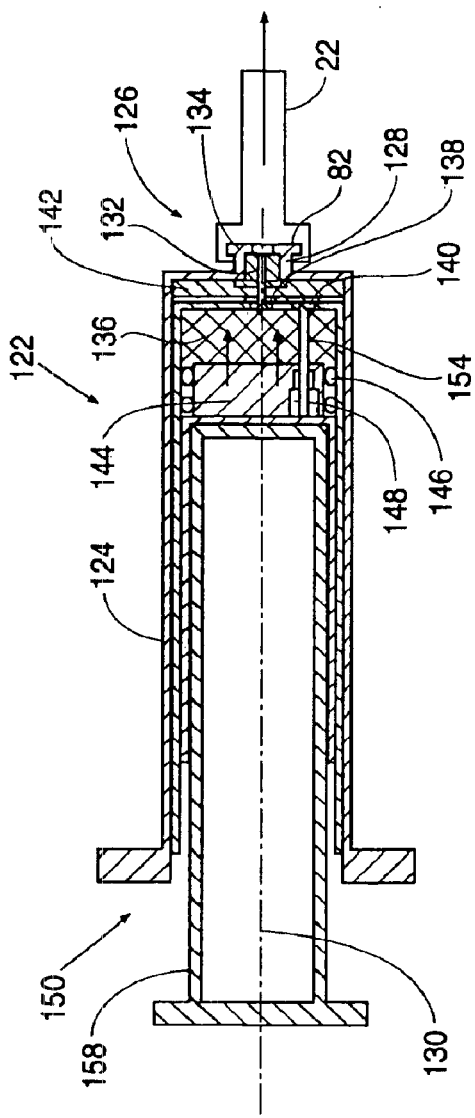

As FIG. 11C shows, continued advancement of the plunger 158, now in contact with the barrier 144, forces the mixing chamber 136 toward the dispensing end 126 of the barrel housing 124, against the elastomeric gasket 142. The gasket 142 compresses, acting as a fluid seal and damping this movement, similar to a spring. As a result of this motion, the puncture spike 132 pierces the first foil seal port 138, opening communication between the mixing chamber 136 and the dispensing port 128. Simultaneously, the offset needle 154 pierces the second foil sealed port 140 and enters the elastomeric gasket 142, which seals the needle 154 from further fluid transfer.

Advancement of the plunger 158 expels the suspension of liquid component 96 and solid component 94 through the dispensing port 128 into the introducer/mixer assembly 22. The mixing chamber 86 brings the liquid and solid components 96 and 94 into further intimate contact to start the chemical reaction between the two.

Figure 18:
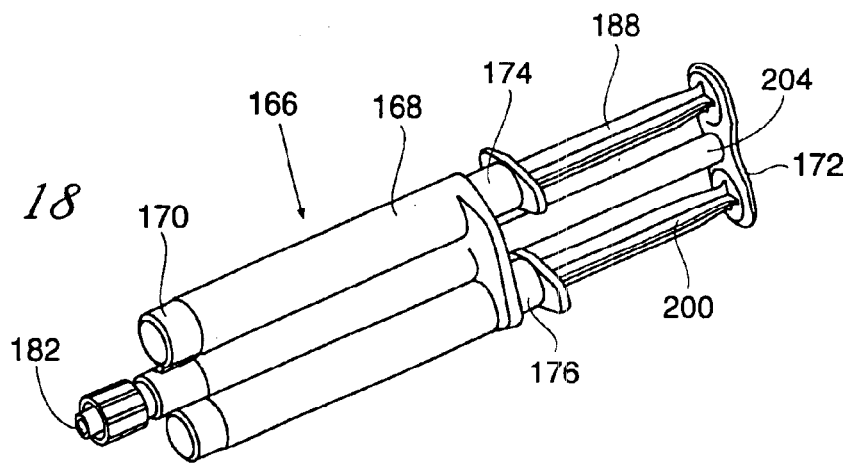
FIG. 18 is a side perspective view of a dual syringe applicator that shows another embodiment of the formative component assembly shown in FIG. 1, through which a solid component and a liquid component for the closure composition are delivered to seal a blood vessel puncture site.

Yet another alternative arrangement for a formative component assembly 18 is shown in FIG. 18. This embodiment provides a unitary holder 166 for holding two or more syringes 174 and 176. The holder 166 can comprise, e.g., a molded plastic part or an assembly of molded plastic parts.

In the illustrated embodiment, the holder 166 includes a main body 168, a nosepiece 170, and a plunger assembly 172. In the illustrated embodiment, the main body 168, the nosepiece 170, and the plunger assembly 172 constitute separately fabricated parts. The main body 168 and the nosepiece are bonded together for use. The plunger assembly 172 is assembled to the main body 168 for sliding action.

The main body 168 holds two conventional syringes 174 and 176. One syringe 174 holds, e.g., the solid component 94 in a liquid suspension. The other syringe 176 holds, e.g., the liquid component 96. The syringes 174 and 176 are inserted for use into side-by-side barrels 190 and 192, which are formed in the main body 168 (see FIG. 19).

Figure 20:
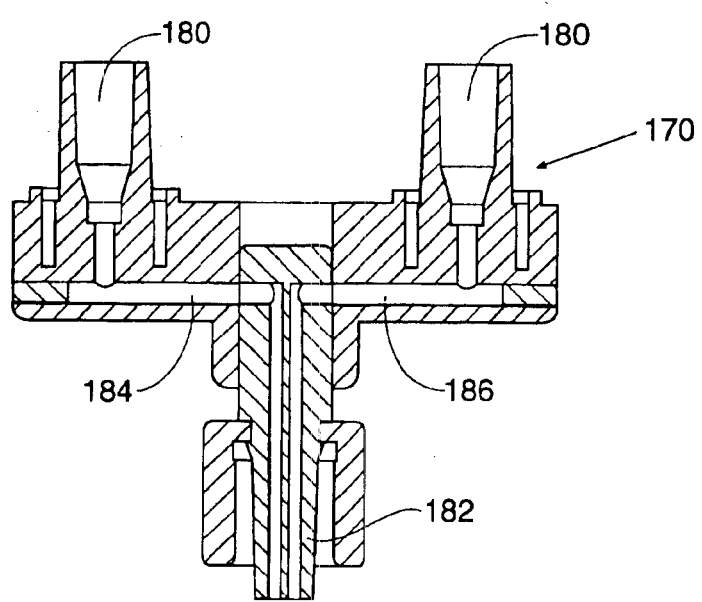
FIG. 20 is a side section view of a nosepiece that forms a part of the dual syringe applicator shown in FIG. 18.

The nosepiece 170 (see FIG. 20) is molded with two threaded female luer fittings 180 and one male luer fitting 182. The female luer fittings 180 independently communicate by passages 184 and 186 with the male luer fitting 182. In use, the male luer fitting 182 is coupled to the luer fitting 80 of the introducer/mixer assembly 22.

Figure 19:
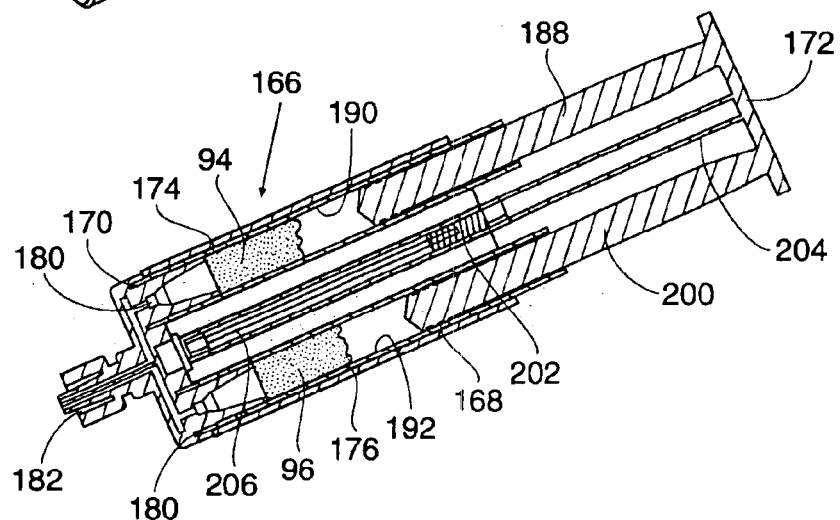
FIG. 19 is a side section view of the dual syringe applicator shown in FIG. 18.

When the nosepiece 170 is bonded to the main body 168, the female luer fittings 180 are each disposed at the end of the barrels 190 and 192 (as FIG. 19 shows). A given syringe 174 or 176 is inserted into a given barrel 190 or 192. The male luer of the syringe 174 or 176 and screwed into fluid flow communication with the female luer fitting 180 at the bottom of that barrel 190 or 192. In this way, the syringes 174 and 176 are readied for use.

The plunger 172 nests with both plungers 188 and 200 of the syringes 174 and 176 inserted for use in the barrels 190 and 192. The plunger 172 is guided by a telescoping tube 204 that rides in a channel 206 in the main body 168 between the two barrels 178 and 179 (see FIG. 19). A spring 202 desirably applies suitable back pressure against the plunger tube 204.

In use, the physician applies thumb pressure to the plunger 172 to advance the syringe plungers 188 and 200 at a constant, equal rate. The solid component 94 (in liquid suspension) and the liquid component 96 are expressed through the passages 184 and 186 of the nosepiece 170 into the male fitting 182. The components 94 and 96 enter the introducer/mixer assembly 22, for mixing in the mixing chamber 86, as already described.

C. The Access Assembly (Alternative Embodiment)

FIGS. 21 and 22 show an alternative embodiment of an access assembly 216. Like the access assembly 16 shown in FIG. 1, the access assembly 216 comprises a catheter assembly 220 and a component introducer/mixer assembly 222.

1. The Catheter Assembly

Like the previously described catheter assembly 20, the catheter assembly 220 comprises a flexible inner catheter body 224 (see also FIG. 23) that is slidably carried within a flexible outer catheter body 226. The outside diameter of the outer catheter body 226 can vary, e.g., from 6 Fr. to 10 Fr. The outside diameter of the outer catheter body 226 is sized to seal the tissue track through which it is introduced, so that its presence is hemostatic.

The inner and outer catheter bodies 224 and 226 can be made from an extruded plastic material, e.g., PEBAX™ material.

The proximal end of the outer catheter body 226 is secured, e.g., by adhesive, to a handle 238. A strain relief sheath 339 desirably encompasses the outer catheter body 226 adjacent the handle 238.

The proximal end of the inner catheter body 224 extends through and beyond the handle 238. The exposed end of the inner catheter body 224 desirably carries a luer fitting 244, so that a flushing fluid can be introduced through the inner catheter body 224. The inside diameter of the inner catheter body 224 defines an interior lumen 254 (see FIG. 23) that is sized to accommodate passage of the guide wire 32.

A carrier 242 is carried on a track 241 in the handle 238 for fore and aft sliding movement. The inner catheter body 224 is adhesively secured within the sliding carrier 242, so that fore and aft movement of the carrier 242 in the track 241 affects sliding movement of the inner catheter body 224 (as FIGS. 21 and 22 show). In response to forward movement of the carrier 242 (as FIG. 21 shows), the inner catheter body 224 slides in a distal direction within the outer catheter body 226. In response to aft movement of the carrier 242 (as FIG. 22 shows), the inner catheter body 224 slides in a proximal direction within the outer catheter body 226.

A spring biased latch mechanism 243 is desirably coupled to the carrier 242. The latch mechanism 243 snap-fits into detents 245 (shown in FIG. 21) at the proximal and distal ends of the track 241, to releasably lock the carrier 242 against movement. Finger pressure releases the spring biased latch mechanism 243 from the detents 245, to release the carrier 242 for movement between the proximal and distal detents 245.

Figure 23:
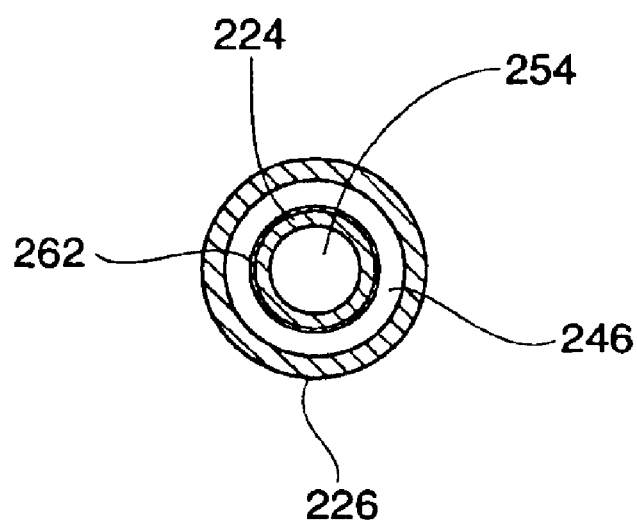
FIG. 23 is a cross section view of the catheter assembly taken generally along line 23—23 in FIG. 22.
Figure 24:
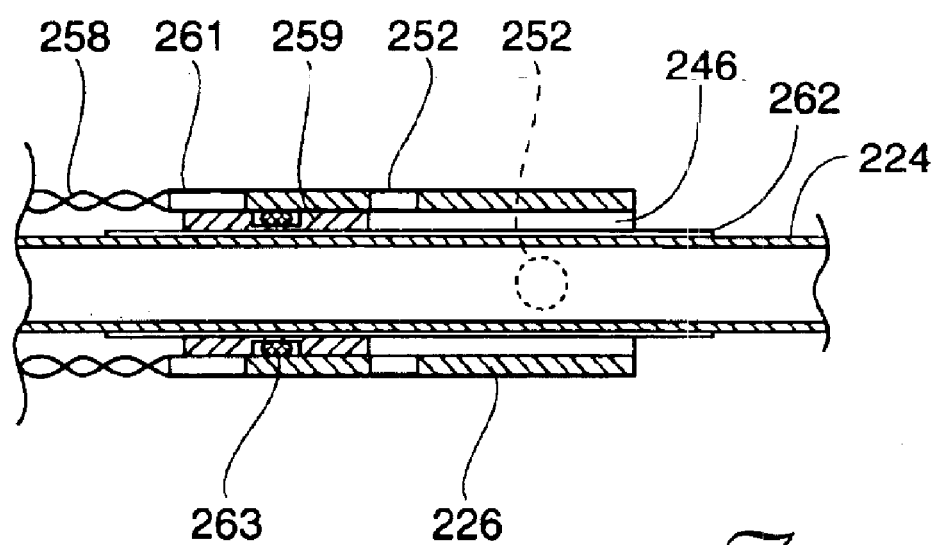
FIG. 24 is an enlarged side section view of the junction between the expandable structure and the outer catheter body of the catheter assembly shown in FIGS. 21 and 22.

As in the catheter assembly 220, an interior passage 246 is defined between the inner and outer catheter bodies 224 and 226 (see FIG. 23). A port 248 on the handle 238 communicates with the passage 246. The port 248 terminates with the component introducer/mixer assembly 222 through intermediate tubing 278. Liquid components introduced through the assembly 222 exit the passage 246 through one or more nozzles 252 formed near the distal end of the outer catheter body 226 (see FIG. 24). As FIGS. 23 and 24 show, a thin wall tube 262 (extruded, e.g., from a polyimide material) desirably covers the inner catheter body 224, to prevent liquid components within the passage 246 from adhesively bonding the inner catheter body 224 to the outer catheter body 226. Free sliding motion of the inner catheter body 224 within the tube 262 is thereby preserved.

As FIGS. 21 and 22 best show, the catheter assembly 220 also includes an expandable structure 258 located near to and distally of the nozzles 252 (see FIG. 24, as well). As before described, the structure 258 desirably comprises an open or woven or braided structure comprising interlaced or intersecting strands or threads, e.g., made from an inert biocompatable polymeric material, such as nylon. The proximal end of the structure 258 is secured (see FIG. 24), e.g., by a fuse joint 261, about a gland member 259 that encircles the thin wall tube 262. As FIG. 24 also shows, the distal end of the outer catheter body 226 is also secured, e.g., by adhesive, to the gland member 259. An o-ring 263 is also desired placed within the gland member 259 to prevent leakage of liquid components from the passage 246 into the interior of the structure 258.

The distal end of the structure 258 is secured, e.g., by adhesive or a shrink-fit sleeve, to a region of the inner catheter body 224 that extends beyond the outer catheter body 226. The inner catheter body 224 also extends a distance distally beyond the structure 258, forming a leader 260 (see FIGS. 21 and 22). In use, the leader 260 is located inside the blood vessel immediately interior to the puncture site 36 (like the leader 60 in FIGS. 14 and 15). In use, the array of nozzles 252 is located outside the blood vessel exterior to the puncture site 36 (like the nozzles 52 in FIG. 15). Sliding movement of the inner catheter body 224 relative to the outer catheter body 26 serves to mechanically expand (see FIG. 22) and collapse (see FIG. 21) the structure 258, so that this desired positioning of the nozzles 252 and leader 260 can be achieved, as previously described.

Since, in the illustrated embodiment, the structure 258 possesses a wall that is open or woven, the structure 258 permits blood flow through it, thereby presenting a minimal disruption of blood flow in the vessel during use. Due to the open or woven configuration of the structure 258, the positioner can be deployed in an expanded state within the artery prior to being seated against the interior of the vessel wall, with minimal disruption of blood flow. This allows the physician to proceed with the deployment and positioning of the structure 258 within the vessel in a deliberate fashion, without being rushed due to ancillary considerations of attendant blood flow disruption. The open structure 258 can be deployed while a patient is in an operating room, and left deployed while the patient is wheeled from the operating room to another suite, where the vessel closure procedure is completed. In this way, the operating room, its staff, and its equipment are made available for another procedure while the vessel closure procedure is completed in another setting by a medically trained person, who need not be a medical doctor.

Desirably, radiopaque marker bands 266 are secured to the proximal and distal ends of the structure 258, as well as to the distal-most end of the leader 260. Preferably, the three markers 266 appear at equidistant intervals when the structure 258 is in its collapsed or stowed condition. Thus, when the structure 258 is in its expanded condition, the markers 266 no longer appear equidistant. In this way, the physician can readily gauge by fluoroscopy the location of the distal-most end of the inner catheter body 224, as well as the distance between the ends of the structure 258 and, thereby, assess the position and configuration of the inner catheter body 224 and the structure 258 near the puncture site 36.

2. The Component Introducer/Mixer Assembly

In the alternative embodiment (see FIGS. 21 and 22), the introducer/mixer assembly 222 includes, communicating with the tubing 278 in the direction of flow into the passage 246, an in-line syringe activated check valve 284, an in-line mixer 286, and an in-line air accumulator 288.

The in-line syringe activated check valve 284 can take various forms. In the illustrated embodiment, the valve 284 takes the form of a conventional, needleless slip luer lock valve made by Qosina (Edgewood, N.Y.), Product Number 80360. The valve 284 is normally closed to prevent back flow of blood or other liquid material through the tubing 278. Back flow of blood, in particular, from the passage 246 is undesirable, as it creates the potential for blood contact and deposits material in the introducer/mixer assembly 222 that can interfere or compete with the desired reaction between the liquid components that form the material composition. Connection of a conventional luer fitting carried by the material composition applicator (for example, fitting 182 shown in FIGS. 18 to 20) opens the valve 284 to allow the introduction of the liquid components that form the material composition.

The components of the material composition come into contact in the liquid state in the in-line mixer 286. In this way, effective mixing can be achieved outside the catheter assembly 220 that is not dependent solely upon the dimensions or lengths of the flow paths within the catheter assembly 220. The mixer 286 comprises a mixing structure, which can vary. For example, the mixer 286 can comprise a spiral mixer manufactured by TAH Industries, Inc. (Robbinsville, N.J.), Part Number 121-090-08.

The in-line air accumulator 288 comprises a chamber that has an interior volume sized to trap air that can reside in the material composition applicator at time of use.

II. The Material Composition

The components 94 and 96 of the material composition can vary. In a preferred embodiment, the solid component 94 comprises an electrophilic (electrode withdrawing) material having a functionality of at least three. The liquid component 96 comprises a solution containing a nucleophilic (electron donator) material and a buffer. When mixed under proper reaction conditions, the electrophilic material and buffered nucleophilic material react, by cross-linking with each other. The cross-linking of the components form the composition. The composition physically forms a mechanical barrier 160 (see FIG. 17), which can also be characterized as a hydrogel.

The type and concentration of the buffer material controls the pH of the liquid and solid components 94 and 96, when brought into contact for mixing. The buffer material desirably establishes an initial pH in numeric terms, as well regulates change of the pH over time (a characteristic that will be called the "buffering capacity").

The barrier composition 160 exhibits desired mechanical properties. These properties include adhesive strength (adhering it to adjacent tissue), cohesive strength (forming a mechanical barrier that is resistant to blood pressure and blood seepage), and elasticity (accommodating the normal stresses and strains of everyday activity). These properties, as well as the relative rapid rate of gelation that can be achieved, serve to provide a fast and effective closure to the vascular puncture site.

The barrier composition 160 is also capable of transforming over time by physiological mechanisms from the solid state to a biocompatible liquid state, which can be cleared by the body, in a process called "degradation."

The time period that begins when the electrophilic, nucleophilic, and buffer components have been mixed and ends when the composition has reached the semi-solid (gel) state will be called the "gelation time." When in this state, the barrier composition 160 possesses sufficient cohesive and adhesive strength to impede blood flow, but still retains a self-sealing property, possessing the capacity to close in upon and seal the tract left by the catheter in the composition when the physician removes the catheter. For sealing a vascular puncture site, the barrier composition 160 preferably possesses a gelation time that is in the range of fifteen to sixty seconds. A gelation time in the range of fifteen to thirty seconds is most preferred. This period allows the components forming the barrier composition 160 to flow first in a liquid state, and then in the semi-solid (gel) state, outward along the axis of the blood vessel. The flow of components during gelation fills surface irregularities in the tissue region of the vascular puncture site 36, before solidification occurs. A gelation time period of between 10 and 40 seconds also falls well within the time period a physician typically needs to manipulate and remove the catheter assembly 20 or 220 after delivery of the components to the puncture site 36. With an experienced physician, the catheter manipulation and removal time period can be as quick as 10 to 40 seconds, but it can extend, due to circumstances, upwards to 2 minutes. With a gelation time falling within the preferred range, the formation of the barrier composition 160 does not require a physician to "watch the clock," but rather attend only to the normal tasks of injecting the material and then manipulating and removing the catheter assembly 20 or 220. With a gelation time falling within the preferred range, it has been discovered that, if the catheter assembly 20 or 220 is removed in 15 seconds to 2 minutes following initial mixing, the barrier composition 160 has reached a physical state capable of performing its intended function, while still accommodating a sealed withdrawal of the catheter assembly 20 or 220. Desirably, after removal of the catheter assembly 20 or 220, the physician applies localized and temporary finger presssure to the skin surface above the barrier composition 160 for a period of about 5 minutes, to aid in the closure of the catheter tract in the composition, as the composition reaches its solid state.

The barrier composition 160 preferably possesses sufficient adhesive strength to prevent dislodging from the arteriotomy, once formed. The composition 16 also has sufficient cohesive strength to prevent rupture under arterial pressure, i.e., up to about 200 mm Hg. The barrier composition 160 seals the arteriotomy for up to 15 days post-application before loss of mechanical properties through degradation, and degrades by 30 to 90 days post-application.

The gelation time (which indicates the rate at which the cross-linking reaction occurs) is controlled, inter alia, by the reaction pH, which the buffer component establishes. The reaction pH controls the reactivity of nucleophilic groups in the second component 96, which react with the electrophilic groups in the first component 94. Generally speaking, the higher the reaction pH is, the larger is the fraction of nucleophilic groups available for reaction with the electrophilic groups, and vice versa.

To achieve a relatively rapid gelation time, a relatively high initial reaction pH (which, for the illustrated components, is above 8) is desirable at the time initial mixing of the components occurs. On the other hand, by the time the mixture is brought into contact with body tissue at the vascular puncture site, it is desirable that mixture possess a more physiologically tolerated pH level (approximately 7.4).

However, it has been discovered that, if the initial reaction pH is too high (which, for the illustrated components, is believed to be a pH approaching about 9), the gelation time may be too rapid to consistently accommodate the time period a physician typically requires to remove the catheter, particularly if the time period approaches the two minute mark. In this instance, by the two minute mark, substantial solidification of the composition can occur, and the composition can lack the cross-linking capacity to close in about the catheter tract left in the composition upon removal of the catheter. Under these circumstances, blood leakage and hematoma formation can result after removal of the catheter.

Achieving and sustaining a reaction pH to meet a targeted gelation time is therefor a critical criteria. It has been discovered that, by purposeful selection of the electrophilic, nucleophilic, and buffer components, (i) an initially high reaction pH can be established that is conducive to rapid gelation, before contact with body tissue occurs, and (ii) the reaction pH can be lowered as gelation progresses, as the mixture is delivered through the catheter into contact with body tissue at the vascular puncture site. At the same time, by purposeful selection of the components, the rate at which the pH is lowered during delivery can be mediated, so that gelation is sustained at a rate that meets the gelation time requirements to achieve the desired in situ formation of the composition 16, one that also possesses sufficent cross-linking capacity to close about the catheter tract following removal of the catheter assembly 20 or 220 after a time period a physician typically needs to perform this task.

A. The Electrophilic Component

In its most preferred form, the electrophilic (electrode withdrawing) material 94 comprises a hydrophilic, biocompatible polymer that is electrophilically derivatized with a functionality of at least three. Examples include poly (ethylene glycol), poly(ethylene oxide), poly(vinyl alcohol), poly(vinylpyrrolidinone), poly(ethyloxazoline), and polylethylene glycol)-co-poly(propylene glycol) block copolymers.

As used herein, a polymer meeting the above criteria is one that begins with a multiple arm core (e.g., pentaerythritol) and not a bifunctional starting material, and which is synthesized to a desired molecular weight (by derivatizing the end groups), such that polymers with functional groups greater than or equal to three constitute (according to gel permeation chromatography—GPC)at least 50% or more of the polymer blend.

The material 94 is not restricted to synthetic polymers, as polysaccharides, carbohydrates, and proteins could be electrophilically derivatized with a functionality of at least three. In addition, hybrid proteins with one or more substitutions, deletions, or additions in the primary structure may be used as the material 94. In this arrangement, the protein's primary structure is not restricted to those found in nature, as an amino acid sequence can be synthetically designed to achieve a particular structure and/or function and then incorporated into the material. The protein of the polymer material 94 can be recombinantly produced or collected from naturally occurring sources.

Preferably, the polymer material 94 is comprised of poly(ethylene glycol) (PEG) with a molecular weight preferably between 9,000 and 12,000, and most preferably 10,500±1500. PEG has been demonstrated to be biocompatible and non-toxic in a variety of physiological applications. The preferred concentrations of the polymer are 5% to 35% w/w, more preferably 5% to 20% w/w. The polymer can be dissolved in a variety of solutions, but sterile water is preferred.

The most preferred polymer material 94 can be generally expressed as compounds of the formula:

PEG-(DCR-CG)$_n$

Where:
DCR is a degradation control region.
CG is a cross-linking group.
$n \geq 3$ The electrophilic CG is responsible for the cross-linking of the preferred nucleophilic material 24, as well as binding the composition 16 to the like material in the surrounding tissue, as will be described later. The CG can be selected to selectively react with thiols, selectively react with amines, or react with thiols and amines. CG's that are selective to thiols include vinyl sulfone, N-ethyl maleimide, iodoacetamide, and orthopyridyl disulfide. CG's that are selective to amines include aldehydes. Non-selective electrophilic groups include active esters, epoxides, oxycarbonylimidazole, nitrophenyl carbonates, tresylate, mesylate, tosylate, and isocyanate. The preferred CG's are active esters, more preferred, an ester of N-hydroxysuccinimide. The active esters are preferred since they react rapidly with nucleophilic groups and have a non-toxic leaving group, e.g., hydroxysuccinimide.

The concentration of the CG in the polymer material 94 can be used to control the rate of gelation. However, changes in this concentration typically also result in changes in the desired mechanical properties of the hydrogel.

The rate of degradation is controlled by the degradation control region (DCR), the concentration of the CG's in the polymer solution, and the concentration of the nucleophilic groups in the protein solution. Changes in these concentrations also typically result in changes in the mechanical properties of the hydrogel, as well as the rate of degradation.

The rate of degradation (which desirably occurs in about 30 days) is best controlled by the selection of the chemical moiety in the degradation control region, DCR. If degradation is not desired, a DCR can be selected to prevent biodegradation or the material can be created without a DCR. However, if degradation is desired, a hydrolytically or enzymatically degradable DCR can be selected. Examples of hydrolytically degradable moieties include saturated di-acids, unsaturated di-acids, poly(glycolic acid), poly(DL-lactic acid), poly(L-lactic acid), poly($\xi$-caprolactone), poly ($\delta$-valerolactone), poly ($\gamma$-butyrolactone), poly(amino acids), poly(anhydrides), poly(orthoesters), poly(orthocarbonates), and poly(phosphoesters), and derivatives thereof. A preferred hydrolytically degradable DCR is gluturate. Examples of enzymatically degradable DCR's include Leu-Gly-Pro-Ala (collagenase sensitive linkage) and Gly-Pro-Lys (plasmin sensitive linkage). It should also be appreciated that the DCR could contain combinations of degradable groups, e.g. poly(glycolic acid) and di-acid.

While the preferred polymer is a multi-armed structure, a linear polymer with a functionality, or reactive groups per molecule, of at least three can also be used. The utility of a given PEG polymer significantly increases when the functionality is increased to be greater than or equal to three. The observed incremental increase in functionality occurs when the functionality is increased from two to three, and again when the functionality is increased from three to four. Further incremental increases are minimal when the functionality exceeds about four.

A preferred polymer may be purchased from Shearwater Polymers Inc. (Product Designation: PEG4SG, having a molecular weight range of between 9000 and 12,000) (which will be called the "Shearwater PEG"). Gel permeation chromatography of the Shearwater PEG reveals that (by nmolecular weight) 59.2% of the Shearwater PEG comprises 4-Arm-PEG polymer.

Alternatively, another preferred polymer may be purchased from SunBio Company ((PEG-SG)$_4$, having a molecular weight of 10,500±1500) (which will be called the "SunBio PEG"). Gel permeation chromotography of the SunBio PEG reveals that (by molecular weight) 3.1% of the SunBio PEG comprises 3-Arm-PEG polymer and 90.7% of the SunBio PEG comprises 4-Arm-PEG polymer. When compared to the Shearwater PEG, it can be seen that the SunBio PEG contains a greater concentration of PEG polymers with a functionality equal to or greater than 3.

B. The Nucleophilic Component

In a most preferred embodiment, the nucleophilic material 96 includes non-immunogenic, hydrophilic proteins. Examples include serum, serum fractions, and solutions of albumin, gelatin, antibodies, fibrinogen, and serum proteins. In addition, water soluble derivatives of hydrophobic proteins can be used. Examples include solutions of collagen, elastin, chitosan, and hyaluronic acid. In addition, hybrid proteins with one or more substitutions, deletions, or additions in the primary structure may be used.

Furthermore, the primary protein structure need not be restricted to those found in nature. An amino acid sequence can be synthetically designed to achieve a particular structure and/or function and then incorporated into the nucleophilic material 96. The protein can be recombinantly produced or collected from naturally occurring sources.

The preferred protein solution is 25% human serum albumin, USP. Human serum albumin is preferred due to its biocompatibility and its ready availability.

The uses of PEG polymers with functionality of greater than three provides a surprising advantage when albumin is used as the nucleophilic material 96. When cross-linked with higher functionality PEG polymers, the concentration of albumin can be reduced to 25% and below. Past uses of difunctional PEG polymers require concentrations of albumin well above 25%, e.g. 35% to 45%. Use of lower concentrations of albumin result in superior tissue sealing properties with increased elasticity, a further desired result. Additionally, 25% human serum albumin, USP is commercially available from several sources, however higher concentrations of human serum albumin, USP are not commercially available. By using commercially available materials, the dialysis and ultrafiltration of the albumin solution, as disclosed in the prior art, is eliminated, significantly reducing the cost and complexity of the preparation of the albumin solution.

To minimize the liberation of heat during the cross-linking reaction, the concentration of the cross-linking groups of the fundamental polymer component is preferably kept less than 5% of the total mass of the reactive solution, and more preferably about 1% or less. The low concentration of the cross-linking group is also beneficial so that the amount of the leaving group is also minimized. In a typical clinical application, about 50 mg of a non-toxic leaving group is produced during the cross-linking reaction, a further desired result. In a preferred embodiment, the CG comprising an N-hydroxysuccinimide ester has demonstrated ability to participate in the cross-linking reaction with albumin without eliciting adverse immune responses in humans.

C. The Buffer Component

In the most preferred embodiment, a PEG reactive ester reacts with the amino groups of the albumin and other tissue proteins, with the release of N-hydroxysuccinimide and the formation of a link between the PEG and the protein. When there are multiple reactive ester groups per PEG molecule, and each protein has many reactive groups, a network of links form, binding all the albumin molecules to each other and to adjacent tissue proteins.

This reaction with protein amino groups is not the only reaction that the PEG reactive ester can undergo. It can also react with water (i.e., hydrolyze), thereby losing its ability to react with protein. For this reason, the PEG reactive ester must be stored dry before use and dissolved under conditions where it does not hydrolyze rapidly. The storage container for the PEG material desirably is evacuated by use of a vacuum, and the PEG material is stored therein under an inert gas, such as Argon or Nitrogen. Another method of packaging the PEG material is to lyophilize the PEG material and store it under vacuum, or under an inert gas, such as Argon or Nitrogen. Lypophilization provides the benefits of long term storage and product stability, as well as allows rapid dissolution of the PEG material in water.

The conditions that speed up hydrolysis tend to parallel those that speed up the reaction with protein; namely, increased temperature; increased concentration; and increased pH (i.e., increased alkali). In the illustrated embodiment, temperature cannot be easily varied, so varying the concentrations and the pH are the primary methods of control.

It is the purpose of the buffer material (which is added to the nucleophilic albumin material 96 prior to mixing with the electrophilic PEG material 94) to establish an initial pH to achieve a desired gelation time, and to sustain the pH as added acid is produced by the release of N-hydroxysuccinimide during cross linking and hydrolysis.

pH is the special scale of measurement established to define the concentration in water of acid (H+) or alkali (OH−) (which, strictly speaking, indicates hydrogen ion activity). In the pH scale, solutions of acid (H+) in water have a low pH, neutrality is around pH 7, and solutions of base (OH−) in water have a high pH. The pH scale is logarithmic. A change of one pH unit (e.g., from pH 9 to pH 10) corresponds to a ten-fold change in concentration (i.e., hydrogen ion activity). Thus, reactions which are increased by alkali, such as hydrolysis of PEG reactive ester, are expected to increase in rate by a factor of ten for each unit increase in pH.

The buffer material is a mixture of molecules, added to the albumin, that can moderate pH changes by reacting reversibly with added acid (H+) or base (OH−). The pH moderating effect can be measured by titration, i.e., by adding increasing amounts of H+ or OH− to the buffer material, measuring the pH at each step, and comparing the pH changes to that of a similar solution without the buffer.

Different buffers exert a maximum pH moderating effect (i.e., the least change in pH with added H+ or OH−) at different pH's. The pH at which a given buffer exerts its maximum pH moderating effect is called its pK.

Even when the pH matches the pK for a given buffer, added acid or base will produce some change in pH. As the pH changes from the pK value, the moderating effect of the buffer decreases progressively (e.g., 67% less at +/−1 pH unit from pK, and 90% less at +/−1.6 pH unit from pK). The moderating effect is also proportional to the buffer concentration. Thus, increasing the buffer concentration increases the ability to moderate pH changes.

The overall buffering effect at any pH is the sum of all buffering species present, and has also been earlier called the buffering capacity. The higher the buffering capacity, the more acid or base must be added to produce a given pH change. Stated differently, the higher the buffering capacity, the longer a given buffer is able to sustain a targeted pH range as acid or base is being added to change the pH.

Albumin itself contains amino, carboxyl, and other groups, which can reversible react with acid and base. That is, albumin itself is a buffer. Also, due to the many different buffering groups that albumin possesses, albumin (e.g., Plasbumin) can buffer over a relatively broad pH range, from below pH 6 to over pH 10. However, it has been discovered that albumin lacks the buffering capacity to, by itself, counterbalance the additional acid (H+) that is produced as a result of hydrolysis and the PEG-albumin cross-linking, given the PEG concentrations required to meet the therapeutic objectives for the composition. Thus, in the preferred embodiment, a buffer material 28 must be added to the albumin to provide the required buffering capacity.

The buffer material must meet several criteria. The buffer material must be (1) non-toxic, (2) biocompatible, (3) possess a pK capable of buffering in the pH range where the desirable gelation time exists, and (4) must not interfere with the reaction of protein with the selected PEG reactive ester. Amine-containing buffers do not meet criteria (4).

To meet criteria (3), the buffer material 28 should have a buffering capacity at the desired cross-linking pH (i.e., as indicated by its pK) that is high enough to counterbalance the additional acid (H+) produced as a result of the cross-linking reaction and hydrolysis, i.e., to keep the pH high enough to achieve the desired gelation time.

It has been discovered, through bench testing, that when cross-linking the Shearwater PEG and SunBio PEG with albumin (Plasbumin), a range of gelation times between an acceptable moderate time (about 30 seconds) to a rapid time (about 2 seconds) can be achieved by establishing a pH range from about 8 (the moderate times) to about 10 (the rapid times). Ascertaining the cross-linking pH range aids in the selection of buffer materials having pK's that can provide the requisite buffering capacity within the pH range.

Phosphate, tris-hydroxymethylaminomethane (Tris), and carbonate are all non-toxic, biocompatible buffers, thereby meeting criteria (1) and (2). Phosphate has a pK of about 7, which provides increased buffering capacity to albumin at pH's up to about 8.5. Tris has a pK of about 8, which provides increased buffering capacity to albumin at pH's up to about 9.5. Addition of Tris to albumin (Plasbumin) at a concentration of 60 mM approximately doubles the buffering capacity of the albumin at a pH near 9. Carbonate has a pK of about 10, and provides increased buffering capacity to albumin in the higher pH ranges. Depending upon the gelation time that is targeted, formulations of Tris, carbonate, and albumin can be used for the buffer material.

EXAMPLE

Carbonate Buffer/Tris Buffer Formulations

Albumin (Human 25%, Plasbumin®-25 manufactured by Bayer Corporation) was buffered using Sodium Carbonate Anhydrous ($Na_2CO_3$) (FW 106.0) ("Carbonate Buffer") mixed with Tris-hydroxymethylaminomethane ($C_4H_{11}NO_3$) (FW 121.1) ("Tris Buffer"). The buffered albumin formulations (2 cc) were mixed with 2 cc of the SunBio PEG (0.45 g of PEG suspended in 2.2 cc of water), to provide 17% w/w PEG solids. The components were mixed in the manner described in Example 1. The pH of the buffered albumin formulation (albumin plus buffer material) and the gelation time (as described above) and were recorded.

Table 1 summarizes the results.

TABLE 1

| Albumin (Human 25%) (ml) | Carbonate Buffer (grams) | Tris Buffer (grams) | pH | Device (Outside Diameter) | Gelling Time (Seconds) |
| --- | --- | --- | --- | --- | --- |
| 20 | 0 | 0.217 | 8.3 | 7 Fr | 11 |
| 20 | 0 | 0.290 | 8.5 | 7 Fr | 7–8 |
| 20 | 0.075 | 0.145 | 8.7 | 7 Fr | 5–6 |
| 20 | 0.138 | 0.145 | 9.0 | 7 Fr | 2–3 |

Table 1 shows rapid gelation times. This is believed due to the larger concentration of multiple functionality PEG in the SunBio PEG, as well as the enhanced buffering capacity that the Tris Buffer (pK 8) provides in the lower pH range (7 to 9). It is also believed that the gelation time will also vary, given the same composition, according to the size and configuration of the delivery device. The addition of Carbonate Buffer (in the pH 8.7 and pH 9 compositions) leads to a further decrease in gelation time, at an increased pH.

Tests of pH 8.3 and pH 8.5 compositions in Table 1 have demonstrated that both composition are successful in sealing femoral puncture sites in sheep in 25 to 40 seconds. The tests also show that either composition possesses sufficient cross-linking capacity to close about the catheter tract following removal of the catheter upwards to two minutes after delivery of the material. Both compositions thereby readily accommodate variations in procedure time.

Tests of pH 8.7 composition in Table 1 have also demonstrated that the composition is successful in sealing femoral puncture sites in sheep in 25 to 40 seconds. The tests also show that, due to the more rapid gelation time, the composition does not possesses sufficient cross-linking capacity to consistently close about the catheter tract following removal of the catheter two minutes after delivery of the material. In this respect, the pH 8.7 composition, despite its faster gelation time, is not as accommodating to changes in procedure time as the pH 8.3 and pH 8.5 compositions, described above. For these reasons, the most preferred range for vessel puncture sealing is between pH 8.3 and pH 8.5.

Further details of the material composition are found in copending U.S. patent application Ser. No. 09/780,014, filed on the same date as this application, and entitled "Systems, Methods, and Compositions for Achieving Closure of Vascular Puncture Sites."

III. Use of the System to Deliver Material Compositions to Close Vascular Puncture Sites Generally speaking, there are four stages in creating the composition to close a given vascular puncture site. These stages are: (1) the introduction stage; (2) the localized compression stage; (3) the hemostasis stage; and (4) the degradation stage.

The phase of the composition differs in each stage, as different physical and physiological events unfold. These different composition phases are, respectively: (1) the liquid phase; (2) the semi-solid (gel) phase; (3) the solid phase; and (4) the re-absorption phase.

A. The Introduction Stage (The Composition Liquid Phase)

In the first stage (see FIG. 14), the physician primes the selected catheter assembly 20 (or 220) and selected introducer/mixing assembly 22 (or 222) with sterile water or saline. The physician then introduces the selected catheter assembly 20 (or catheter assembly 220) through the tissue track 34 partially into the blood vessel through the vascular puncture 36. As FIG. 14 shows, the structure 58 is in a collapsed condition at this stage. The remainder of the discussion assumes that catheter assembly 20 and introducer/mixing assembly 22 have been selected for use.

Typically, the catheter assembly 20 is introduced along a guide wire 32. As earlier explained and as shown in preceding FIGS. 12 and 13, the guide wire 32 will have been previously introduced percutaneously, through a wall of the blood vessel, to guide passage of a desired therapeutic or diagnostic instrument 30 into the blood vessel. As also previously explained, the diameter of the outer catheter body 26 of the catheter assembly 20 is preferably sized to seal, but not enlarge, the tissue track 34. In other words, the outside diameter of the outer catheter body 26 substantially matches the outside diameter of the vascular introducer 28 (by now retracted).

As FIG. 15 shows, the structure 58 is expanded within the blood vessel (as previously described). The physician applies back pressure on the catheter assembly 20, bringing the expanded structure into contact with the interior of the vessel wall. By gauging the back pressure, the physician locates the nozzles 52 outside the puncture site 36, as FIG. 15 shows. The physician links the dispenser assembly 18 through the introducer/mixer assembly 22 to the catheter assembly 20 (as shown in FIG. 7).

In a most preferred embodiment, the solid component comprises 4-arm poly(ethylene glycol) tetra-succinimidyl glutarate, MW 10,500±1500 (from SunBio). The liquid component comprises 25% w/w human serum albumin, USP supplemented with Tris Buffer to obtain a pH of between 8.0 and 8.7, and most preferably between 8.3 and 8.5. This composition is described in Table 1 of the foregoing Example.

Figure 16:
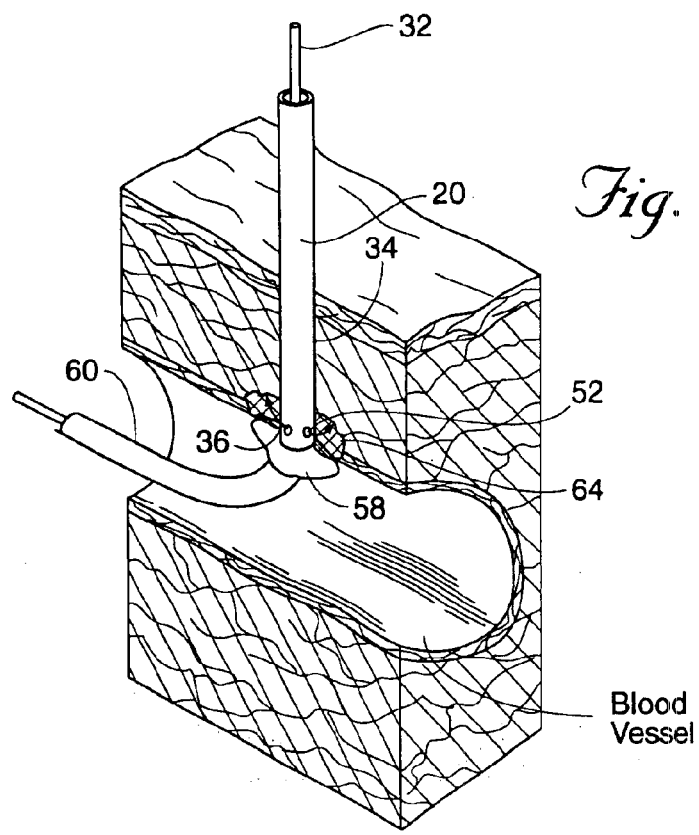
FIG. 16 is a diagrammatic view of the blood vessel puncture site shown in FIG. 15, as the closure composition is being delivered through the closure composition delivery nozzles outside the blood vessel.

Operation of the dispenser assembly 18, as previously described, expresses the components, while in liquid form, through the mixing chamber 86 and down the catheter assembly 20 toward the nozzles 52. The gelating components 64 flow out the nozzles 52 and into the subcutaneous tissue surrounding the vessel, as FIG. 16 shows. The catheter assembly 20, which is sized to seal the tissue track, blocks substantial flow in a path up the tissue track 34. Thus, the gelating components 64 are directed in a flow radially away from the axis of the catheter assembly 20 and along the axis of the vessel, as FIG. 16 shows.

In FIG. 16, the nozzles are arranged in a circumferentially spaced array, as shown in FIG. 6A. The array is desirably close to the puncture site 36. If the blood vessel has be accessed before in the same region, scar tissue may be present adjacent to the puncture site, and the nozzles 52, arranged as shown in FIG. 6A, may reside in the scar tissue region. The scar tissue could interfere with the passage of the gelating components 64. In this circumstance, it may be desirable to arrange the nozzles 52 in the superior-inferior pattern shown in FIG. 6B, in which another array of superior nozzles 52B (located free of the scar tissue region) are axially spaced away from the array of inferior nozzles 52A (located within the scar tissue region). In this arrangement, it is desirable to size the superior nozzles 52B smaller than the inferior nozzles 52A. For example, the superior nozzles 52B can have an outside diameter of about 0.020 inches, whereas the inferior nozzles 52A can have an outside diameter of about 0.035 inches. The differential sizing of the nozzles 52A and 52B creates differential flow, creating a preferred normal flow path (of least flow resistance) through the inferior nozzles 52A, but allowing alternative flow through the superior nozzles 52B should increased flow resistance be encountered through the inferior nozzles 52A due to surrounding tissue morphology.

The spacing between the nozzles 52A and 52B can also vary. For example, the inferior nozzles 52A can be spaced from the structure 58 by 3 to 10 mm, whereas the superior nozzles 52B can be further spaced 5 to 15 mm from the structure 58.

The size of the catheter assembly 20 is selected according to the outside diameter of the introducer sheath 28 used during the preceding therapeutic or diagnostic procedure, during which the arteriotomy was made. For example, a 6 Fr introducer sheath 28 typically has an outside diameter of 7 Fr, so a 7 Fr diameter catheter assembly 20 is selected to seal the arteriotomy after removal of the introducer sheath 28. The composition 64 is delivered in a liquid state adjacent to the arteriotomy, while the catheter assembly 20 prevents the liquid from filling the tissue track 34. This feature ensures that the material composition remains at the arteriotomy for maximum efficacy.

The incoming flow, directed in this manner, creates a tissue space about the puncture site 36 along the axis of the vessel. The gelating components 64 fill this space.

In the gelation process, the electrophilic component and the nucleophilic component cross-link, and the developing composition 64 gains cohesive strength to close the puncture site 36. The electrophilic component also begins to cross-link with nucleophilic groups on the surrounding tissue mass. Adhesive strength forms, which begins to adhere the developing composition to the surrounding tissue mass.

During the introduction stage, before internal cohesive and tissue adhesive strengths fully develop, a portion of the gelating components 64 can enter the blood vessel through the puncture site 36. Upon entering the blood stream, the gelating components 64 will immediately experience physical dilution. The dilution expands the distance between the electrophilic component and the nucleophilic component, making cross-linking difficult. In addition, the diluted components now experience an environment having a pH (7.3 to 7.4) lower than the an effective reactive pH for cross-linking (which is above 8) (as an example, a typical gelation time at pH 8.3 is about 15 to 20 seconds, whereas a typical gelation time at pH 7.4 is over 10 minutes). As a result, incidence of cross-linking within the blood vessel, to form the hydrogel composition, is only a fraction of what it is outside the vessel, where gelation continues.

Furthermore, the diluted electrophilic component will absorb nucleophilic proteins present in the blood. This reaction further reduces the reactivity of the electrophilic component. In blood, the diluted electrophilic component is transformed into a biocompatible, non-reactive entity, which can be readily cleared by the kidneys and excreted. The diluted nucleophilic component 12 is a naturally occurring protein that is handled in normal ways by the body.

The Introduction Stage (The Composition Liquid Phase) preferably last about 5 to 30 seconds from the time the physician begins to mix the components 94 and 96.

B. The Localized Compression Stage
(The Semi-Solid Composition Phase)

The second stage begins after the physician has delivered the entire prescribed volume of components 94 and 96 to the tissue mass of the vessel puncture site 36 and allowed the cross-linking of the components 94 and 96 to progress to the point where a semi-solid gel occupies the formed tissue space.

Figure 17:
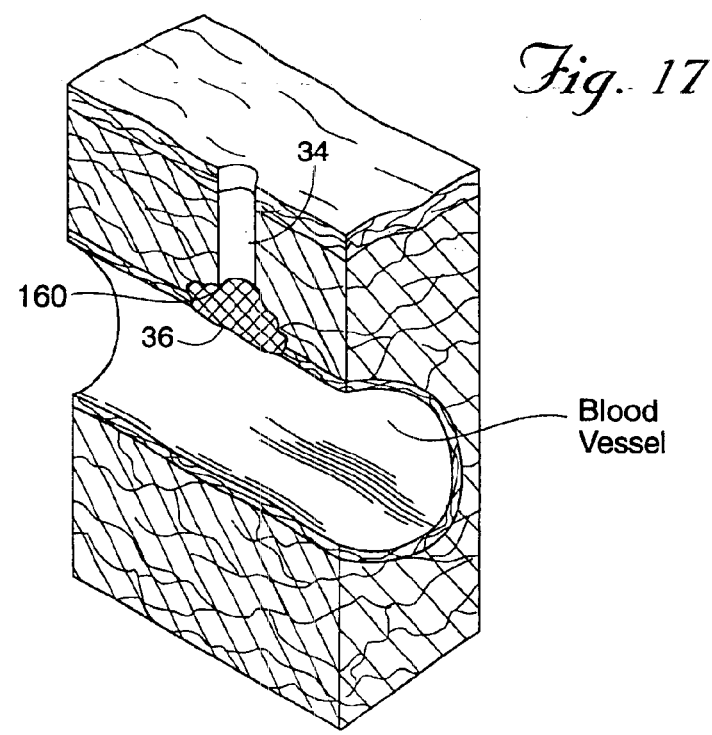
FIG. 17 is a diagrammatic view of the blood vessel puncture site shown in FIG. 16, after removal of the vascular puncture site access assembly and after the closure composition has formed a barrier to seal the puncture site.

At this point (as FIG. 17 shows), the physician collapses the structure 58 and withdraws the catheter assembly 20 and guide wire 32 from the tissue track 34. The physician now simultaneously applies localized and temporary compression to the exterior skin surface surrounding the tissue track 34.

The application of localized pressure serves two purposes. It is not to prevent blood flow through the tissue track 34, as cross-linking of the components 94 and 96 has already proceeded to create a semi-solid gel having sufficient cohesive and adhesive strength to impede blood flow from the puncture site. Rather, the localized pressure serves to compress the tissue mass about the semi-solid gel mass. This compression brings the semi-solid gel mass into intimate contact with surrounding tissue mass, while the final stages of cross-linking and gelation take place.

Under localized compression pressure, any remnant catheter track existing through the gel mass will also be closed.

Under localized compression pressure, surface contact between the adhesive gel mass and tissue is also increased, to promote the cross-linking reaction with nucleophilic groups in the surrounding tissue mass. Adhesive strength between the gel mass and tissue is thereby allowed to fully develop, to firmly adhere the gel mass to the surrounding tissue as the solid composition 160 forms in situ.

During this stage, blood will also contact the vessel-side, exposed portion of the gel mass, which now covers the tissue puncture site. The electrophilic component will absorb nucleophilic proteins present in the blood, forming a biocompatible-surface on the inside of the vessel.

The Localized Compression Stage (The Composition Semi-Solid (Gel) Phase) preferably last about 3 to 10 minutes from the time the physician withdraws the catheter assembly 30.

C. The Hemostasis Stage
(The Composition Solid Stage)

At the end of the Localized Compression Stage, the solid composition 160 has formed (as FIG. 17 shows). Hemostasis has been achieved. The individual is free to ambulate and quickly return to normal day-to-day functions.

The mechanical properties of the solid composition 160 are such to form a mechanical barrier. The composition 160 is well tolerated by the body, without invoking a severe foreign body response.

The mechanical properties of the hydrogel are controlled, in part, by the number of crosslinks in the hydrogel network as well as the distance between crosslinks. Both the number of crosslinks and the distance between crosslinks are dependent on the functionality, concentration, and molecular weight of the polymer and the protein.

Functionality, or the number of reactive groups per molecule, affects the mechanical properties of the resulting hydrogel by influencing both the number of and distance between crosslinks. As discussed previously, the utility of a given polymer significantly increases when the functionality is increased to be greater than or equal to three. The observed incremental increase in functionality occurs when the functionality is increased from two to three, and again when the functionality is increased from three to four. By increasing the functionality of the polymer or protein at a constant concentration, the concentration of crosslinking groups available for reaction are increased and more crosslinks are formed. However, increased mechanical properties cannot be controlled with functionality alone. Ultimately, the steric hindrances of the protein or polymer to which the reactive groups are attached predominate and further changes in the mechanical properties of the hydrogel are not observed. The effect of functionality is saturated when the functionality reaches about four.

The concentration of the protein and polymer also affect the mechanical properties of the resulting hydrogel by influencing both the number of and distance between crosslinks. Increasing the protein and polymer concentration increases the number of available crosslinking groups, thereby increasing the strength of the hydrogel. However, decreases in the elasticity of the hydrogel are observed as the concentration of the protein and polymer is increased. The effects on the mechanical properties by concentration are limited by the solubility of the protein and polymer.

The polymer and protein molecular weight affects the mechanical properties of the resulting hydrogel by influencing both the number of and distance between crosslinks. Increasing the molecular weight of the protein and polymer decreases the number of available crosslinking groups, thereby decreasing the strength of the hydrogel. However, increases in the elasticity of the hydrogel are observed with increasing molecular weight of the protein and polymer. Low molecular weight proteins and polymers result in hydrogels that are strong, but brittle. Higher molecular weight proteins and polymers result in weaker, but more elastic gels. The effects on the mechanical properties by molecular weight are limited by the solubility of the protein and polymer. However, consideration to the ability of the body to eliminate the polymer should be made, as large molecular weight polymers are difficult to clear.

D. The Degradation Stage
(The Composition Re-Absorption Stage)

Over a controlled period, the material composition is degraded by physiological mechanisms. Histological studies have shown a foreign body response consistent with a biodegradable material, such as VICRYL™ sutures. As the material is degraded, the tissue returns to a quiescent state. The molecules of the degraded genus hydrogel composition are cleared from the bloodstream by the kidneys and eliminated from the body in the urine. In a preferred embodiment of the invention, the material loses its physical strength during the first fifteen days, and totally resorbs in about four to eight weeks, depending upon the person's body mass.

The features of the invention are set forth in the following claims.

We claim:

1. An assembly for introducing a closure material to seal a puncture site in a blood vessel, the closure material comprising a mixture of first and second components which, upon mixing, react to form a solid closure material composition, the assembly comprising a catheter for passage through a tissue puncture track and having a distal end, at least one nozzle located adjacent the distal end, and a catheter lumen in the catheter to convey the first and second components for dispensing through the at least one nozzle, an introducer assembly adapted to communicate with the catheter lumen for dispensing the first and second components into the catheter lumen, the introducer assembly including a mixing chamber including an interior mixing structure to bring the first and second components into a mixed condition before entering the catheter lumen, and a structure carried by the catheter distal to the at least one nozzle and being arranged for expansion within the blood vessel to resist outward passage through the puncture site and to thereby located the at least one nozzle outside the blood vessel adjacent the puncture site.

2. An assembly according to claim 1 wherein the catheter is sized to block flow of fluid from the nozzle into a substantial part of the tissue puncture, whereby the solid closure material composition forms a localized in situ closure adjacent the vessel puncture site to seal the vessel puncture site.

3. An assembly according to claim 1 further including a mechanism to operate the structure between a collapsed condition, permitting passage through the puncture site into the blood vessel, and an expanded condition, resisting passage through the puncture site.

4. An assembly according to claim 3 wherein the mechanism includes an element to selectively lock the structure in a desired expanded, collapsed, or intermediate condition.

5. An assembly according to claim 1 wherein the introducer assembly includes an air vent.

6. An assembly according to claim 1 wherein the introducer assembly includes a closure composition test chamber.

7. An assembly as in claim 1 wherein the structure comprises a wall defining an interior and exterior of the structure, the structure comprising an open configuration allowing blood flow through the wall of the structure.

* * * * *

UNITED STATES PATENT AND TRADEMARK OFFICE
CERTIFICATE OF CORRECTION

| | |
|---|---|
| PATENT NO. | : 6,949,114 B2 |
| APPLICATION NO. | : 09/780843 |
| DATED | : September 27, 2005 |
| INVENTOR(S) | : Charles F. Milo et al. |

It is certified that error appears in the above-identified patent and that said Letters Patent is hereby corrected as shown below:

On the title page item (56), under "Other Publications" insert --Transactions: Society for Biomaterials: 'Proteolytically Degradable Hydrogels'; West et al.; 1997.--

Signed and Sealed this

Nineteenth Day of February, 2008

JON W. DUDAS
*Director of the United States Patent and Trademark Office*